(12) United States Patent
Pearlman et al.

(10) Patent No.: US 9,603,839 B2
(45) Date of Patent: Mar. 28, 2017

(54) THIOREDOXIN PROTEIN INHIBITORS AND USES THEREOF

(71) Applicant: Case Western Reserve University, Cleveland, OH (US)

(72) Inventors: Eric Pearlman, Lakeline, OH (US); Sixto M. Leal, Jr., Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/395,377

(22) PCT Filed: Apr. 18, 2013

(86) PCT No.: PCT/US2013/037188
§ 371 (c)(1),
(2) Date: Oct. 17, 2014

(87) PCT Pub. No.: WO2013/158892
PCT Pub. Date: Oct. 24, 2013

(65) Prior Publication Data
US 2015/0306073 A1    Oct. 29, 2015

Related U.S. Application Data

(60) Provisional application No. 61/635,015, filed on Apr. 18, 2012.

(51) Int. Cl.
| | | |
|---|---|---|
| *A61K 31/4164* | (2006.01) | |
| *A61K 9/00* | (2006.01) | |
| *A61K 45/06* | (2006.01) | |
| *A61K 31/10* | (2006.01) | |

(52) U.S. Cl.
CPC ........ *A61K 31/4164* (2013.01); *A61K 9/0048* (2013.01); *A61K 31/10* (2013.01); *A61K 45/06* (2013.01)

(58) Field of Classification Search
CPC ... A61K 31/4164; A61K 45/06; A61K 9/0048
See application file for complete search history.

(56) References Cited

U.S. PATENT DOCUMENTS

2009/0280100 A1    11/2009    Yodoi et al.

FOREIGN PATENT DOCUMENTS

WO    2005007108 A2    1/2005

OTHER PUBLICATIONS

Berdicevsky et al. Mycoses, (2009), 52(4), p. 313-317.*
Welsh et al. Molecular Cancer Therapeutics, (2003), 2, p. 235-243.*
Fekkar et al. The Journal of Infectious Diseases, (2012), 205, p. 1163-1172.*
Patel et al. Mycoses, (2011), 54(3), p. 183-188. (Provided to the Office by Applicants).*
Berdicevsky, I., et al., "Preliminary Study of activity of the thioredoxin inhibitor pleurotin against Trichophyton Mentagrophytes: a Novel anti-dermatophyte possibility", Mycoses, 2009, vol. 52, Issue 4, pp. 313-317.
Mukherjee, A., et al., "Cytotoxic and antiangiogenic activity of AW464 (NSW 706704), a novel thioredoxin inhibitor: an in vitro study", British Journal of Cancer, 2005, vol. 92, No. 2, pp. 350-358.
Patel, G.A., et al., "Tinea capitis: still an unsolved problem?", Mycoses, 2011, vol. 54, Issue 3, pp. 183-188.

* cited by examiner

*Primary Examiner* — Yong Chu
(74) *Attorney, Agent, or Firm* — Tarolli, Sundheim, Covell & Tummino LLP

(57) ABSTRACT

A method of treating a fungal infection in a subject including administering to the subject a therapeutically effective amount of a thioredoxin protein inhibitor to treat the fungal infection in the subject.

24 Claims, 10 Drawing Sheets

THIOREDOXIN PROTEIN INHIBITORS AND USES THEREOF

RELATED APPLICATION

This application claims priority from U.S. Provisional Application No. 61/635,015, filed Apr. 18, 2012, the subject matter of which is incorporated herein by reference in its entirety.

GOVERNMENT FUNDING

This invention was made with government support under EYRO1 18612 awarded by the National Institutes of Health. The United States government has certain rights to the invention.

TECHNICAL FIELD

This application relates to thioredoxin protein inhibitors for use in the treatment of fungal infections.

BACKGROUND

Pathogenic fungi occur worldwide and can cause diseases in humans, animals and plants. Fungal infections in humans range from superficial, e.g., skin surface to deeply invasive type or disseminated infection. Some of such infections especially those that are disseminated are fatal. Thus, fungal diseases can be divided into the life-threatening systemic infections, such as histoplasmosis, systemic candidiasis, aspergillosis, blastomycosis, coccidioidomycosis, paracoccidioidomycosis, and cryptococcosis, and more common ones which are non-life-threatening, like dermatophyte (ringworm) infections, including tinea pedis (athlete's foot), tinea cruris (jock itch), candidiasis, and actinomycosis.

The life-threatening fungal infections are a growing problem not only for immunosuppressed or immunocompromised individuals but also in individuals with viral infections, such as cytomegalovirus (CMV), and influenza, for cancer patients receiving chemotherapy or radiotherapy, for transplant patients receiving antirejection agents, and for patients that have received toxic chemicals, metals and radiation exposure. Fungal opportunistic infections, such as candidiasis, cryptococcosis, and histoplasmosis, occur frequently in patients with AIDS. Among the opportunistic infections, fungal infections caused by *Pneumocystis, Candida, Cryptococcus,* or *Histoplasma* are very common and prevalence can be as high as 85% among HIV-infected individuals. The incidence of systemic fungal infections increased 600% in teaching hospitals and 220% in non-teaching hospitals during the 1980's. The most common clinical isolate is *Candida albicans* (comprising about 19% of all isolates). Nearly 40% of all deaths from hospital-acquired infections were due to fungi.

The treatment of fungal infections has lagged behind bacterial chemotherapy. There are substantially fewer antifungal drugs than antibacterial drugs. The majority of known antifungal agents fall into one of three main groups. The major group includes polyene derivatives, including amphotericin B and the structurally related compounds nystatin and pimaricin, which are only administered intravenously. These are broad-spectrum antifungals that bind to ergosterol, a component of fungal cell membranes, and thereby disrupt the membranes, leading to cell death. Amphotericin B is usually effective for systemic mycoses, but its administration is limited by toxic effects that include fever and kidney damage, and other accompanying side effects, such as anemia, low blood pressure, headache, nausea, vomiting and phlebitis. The unrelated antifungal agent flucytosine (5-fluorocytosine), an orally absorbed drug, is frequently used as an adjunct to amphotericin B treatment for some forms of candidiasis and cryptococcal meningitis. Its adverse effects include bone marrow depression with leukopenia and thrombocytopenia.

The second major group of antifungal agents includes azole derivatives which impair synthesis of ergosterol via lanosterol demethylase and lead to accumulation of metabolites that disrupt the function of fungal membrane-bound enzyme systems (e.g., cytochrome P450) and inhibit fungal growth. Significant inhibition of mammalian P450 results in important drug interactions. This group of agents includes ketoconazole, clotrimazole, miconazole, econazole, butoconazole, oxiconazole, sulconazole, terconazole, fluconazole and itraconazole. These agents may be administered to treat systemic mycoses. Ketoconazole, an orally administered imidazole, is used to treat nonmeningeal blastomycosis, histoplasmosis, coccidioidomycosis and paracoccidioidomycosis in non-immunocompromised patients, and is also useful for oral and esophageal candidiasis. Adverse effects include rare drug-induced hepatitis; ketoconazole is also contraindicated in pregnancy. Itraconazole appears to have fewer side effects than ketoconazole and is used for most of the same indications. Fluconazole also has fewer side effects than ketoconazole and is used for oral and esophageal candidiasis and cryptococcal meningitis. Miconazole is a parenteral imidazole with efficacy in coccidioidomycosis and several other mycoses, but has side effects including hyperlipidemia and hyponatremia.

The third major group of antifungal agents includes allylamnines-thiocarbamates, which are generally used to treat skin infections. This group includes tolnaftate and naftifine. Another antifungal agent is griseoflulvin, a fungistatic agent which is administered orally for fungal infections of skin, hair or nails that do not respond to topical treatment.

Limitations of current therapeutic options include: inadequate spectrum of activity, lack of efficacy due to growing resistance, poor safety profile, multiple drug interactions, inadequate pharmacokinetic profile, and excessive cost. Development of antifungal agents is a challenge because there are very few potential drug targets unique to fungi. Experts in fungal field agree that new drugs needs to be developed. Three novel azoles that offer improved potency and a wide spectrum of activity are in late-stage development: voriconazole, posaconazole, and ravuconazole. Another new class of agents, the candins—are a novel generation of cell-wall active semisynthetic 1,3 beta-glucan inhibitors—caspofungin, micafungin, and anidulafungin. There is also so-called Nyotran, a novel liposomal formulation of nystatin. In addition, a new class of protein synthesis inhibitors, the sordarins, are in preclinical development. Resistance to antifungals has become more apparent in recent years and may worsen with the increase in prophylatic therapy even with new drugs being developed.

SUMMARY

Embodiments described herein relate to methods of treating a fungal infection, and particularly relates to methods of treating a fungal infection in a subject. The method includes administering to a fungal cell a therapeutically effective amount of a thioredoxin protein inhibitor to treat the fungal infection in the subject. The thioredoxin protein inhibitor can have a molecular weight of less than about 350 g/mole. In some embodiments, the thioredoxin inhibitor can include an asymmetrical or symmetrical disulfide and the formula $R_1$—S—S—$R_2$, wherein $R_1$ and $R_2$ are each selected from the group consisting of a substituted or unsubstituted alkyl, arylalkyl, imidazole, thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone; and pharmaceutically acceptable salts thereof.

In other embodiments, the thioredoxin protein inhibitor can include a asymmetrical or symmetrical disulfide having a molecular weight of less than about 350 g/mole and the formula $R_1$—S—S—Y—S—S—$R_2$, wherein $R_1$, $R_2$, and Y are each independently selected from the group consisting of a substituted or unsubstituted alkyl, arylalkyl, imidazole, thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone; and pharmaceutically acceptable salts thereof.

In some embodiments, Y can be selected from the group consisting of hydrogen, a substituted or unsubstituted alkyl, hydroxyalkyl, arylalkyl, and thiadiazoles. In other embodiments, $R_1$ and $R_2$ may each be selected from the group consisting of:

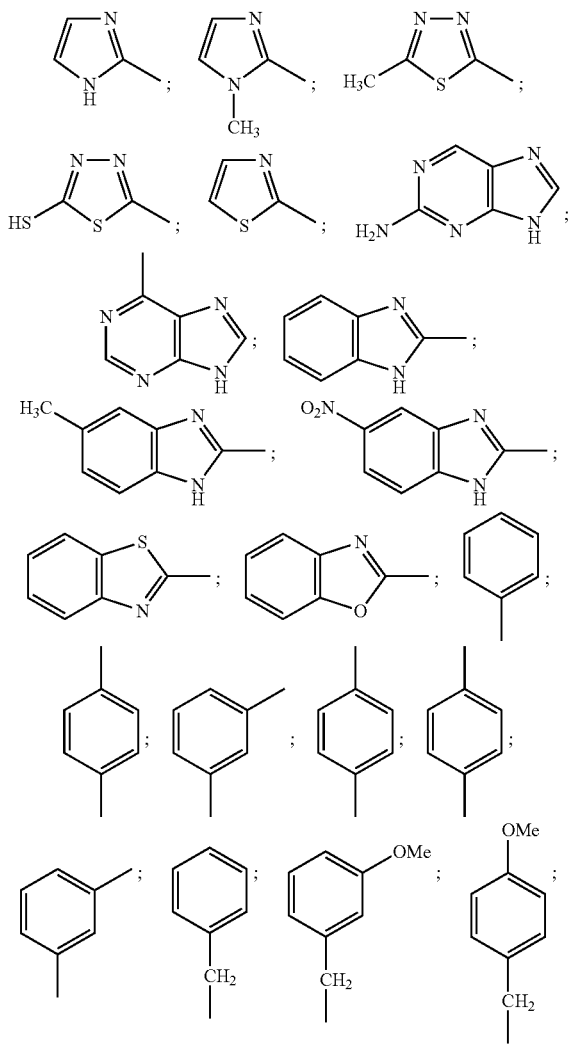

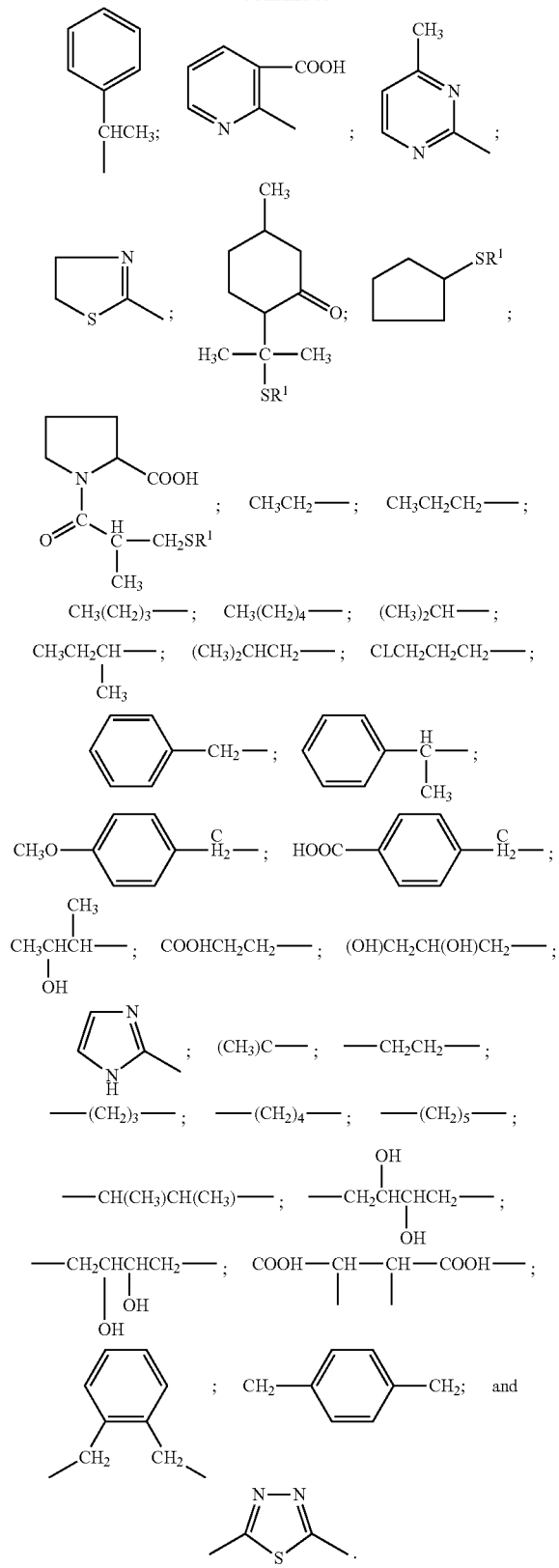

In some embodiments, the thioredoxin protein inhibitor includes an asymmetric disulfide compound having the general formula (I):

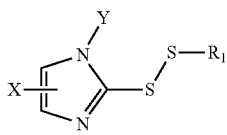

(I)

or a pharmaceutically acceptable salt thereof, wherein $R_1$ and Y are each independently selected from the group consisting of a hydrogen, a substituted or unsubstituted alkyl, arylalkyl, imidazole thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone; and wherein X is selected from the group consisting of hydrogen, alkyl, alkoxy, hydroxyl, carboxy, carbaldehyde, amino, halo, keto, nitro and combinations thereof.

In certain embodiments, the thioredoxin protein inhibitor of formula (I) has the formula:

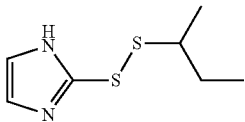

or a pharmaceutically acceptable salt thereof.

The therapeutically effective amount of a thioredoxin protein inhibitor can include an amount effective to inhibit the YAP1-regulated thioredoxin anti-oxidative stress response in a fungal cell, such as a fungal cell in a subject.

In some embodiments, the fungal infection is a fungal infection of the subject and is selected from the group consisting of corneal, lung, skin/nail, mucosal, systemic fungal infections and combinations thereof. The fungal infection can be selected from an *Alternaria, Aspergillus, Candida, Curvularia, Fusarium,* or *Histoplasma* fungal infection.

In certain embodiments, the fungal infection can include a corneal fungal infection. The corneal fungal infection can include a corneal fungal infection related to *Aspergillus, Fusarium, Curvularia,* or *Alternaria*. In some aspects, the corneal fungal infection can be associated with corneal inflammation.

In some embodiments, the subject does not have a fungal infection, but is at risk of developing a fungal infection. The subject may also be a neutropenic subject.

In some embodiments, the thioredoxin protein inhibitor is administered to the subject topically. In other embodiments, the thioredoxin protein inhibitor is administered to the subject in an ophthalmic preparation. In some embodiments, the thioredoxin protein inhibitor is administered to the subject in conjunction with one or more additional therapeutic agents. The one or more additional therapeutic agents can include, for example, a fungal iron acquisition inhibitor, an antibiotic, an antiviral agent, or an antifungal agent.

cultured for 6 hours to obtain hyphae and subsequently coincubated with a sublethal MOI of human neutrophils ($1\times10^5$) for 16 hours; (B) a graph quantifying fungal growth by calcofluor white staining and fluorometry of the Δsod1/2/3, WT Ku80; (C) a graph quantifying fungal growth by calcofluor white staining and fluorometry of ΔcatA, Δcat1/2, WT G10; (D) a graph quantifying fungal growth by calcofluor white staining and fluorometry of ΔgliP, gliPR, WT B-5233; and (E) a graph quantifying fungal growth by calcofluor white staining and fluorometry of ΔgliZ, gliZR, ΔlaeA, laeA-R, WT Af293 *A. fumigatus* strains 16 hours after exposure to human neutrophils.

Figure 8:
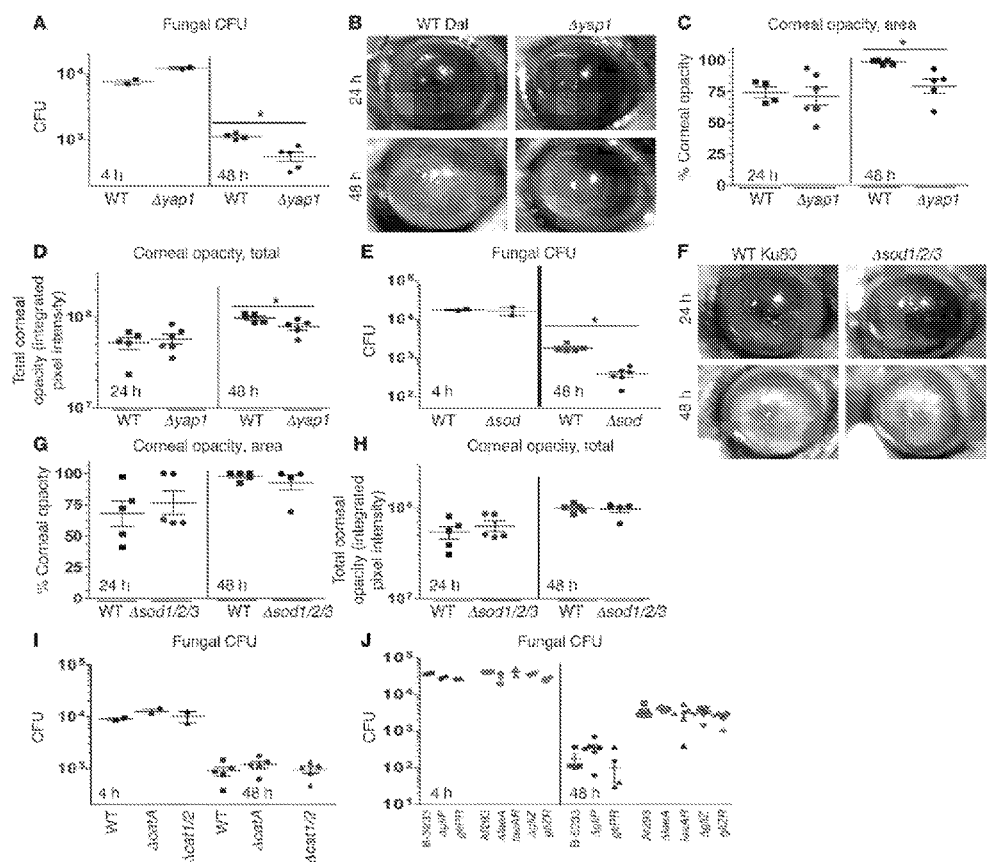

FIGS. 8(A-J) illustrates: (A) a graph quantifying fungal CFU at 4 and 48 hours of C57BL/6 mice infected with 40,000 *A. fumigatus* conidia isolated from either Δyap1 or the WT Dal1 strain; (B) images of the eyes at 24 and 48 hours after infection; (C) a graph quantifying orneal opacity area of the eyes; (D) a graph quantifying total corneal opacity of the eyes; (E) a graph quantifying fungal CFU at 4 and 48 hours after infection of C57BL/6 mice with either the Δsod1/2/3 or the WT Ku80 strain; (F) images showing the eyes at 24 and 48 hours after infection; (G) a graph quantifying corneal opacity area; (H) a graph quantifying total corneal opacity; (I) a graph quantifying CFU levels of corneas of C57BL/6 mice infected with ΔcatA, Δcat1/2, or the WT G10 strain; (J) a graph quantifying CFU levels of corneas of C57BL/6 mice infected with ΔgliZ, gliZR, ΔlaeA, laeA-R, WT Af293 or ΔgliP, gliPR, WT B-5233.

Figure 9:
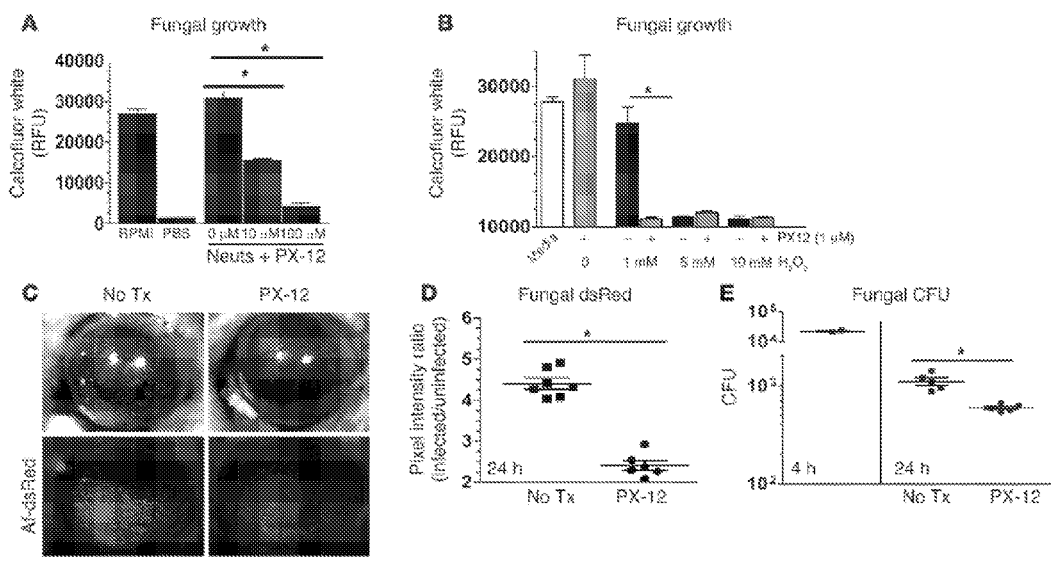

FIGS. 9(A-E) illustrate: (A) a graph quantifying fungal growth by calcofluor white staining and fluorometry of hyphae coincubated with a sublethal MOI of human neutrophils in RPMI or neutrophils plus varying doses of the thioredoxin inhibitor PX-12; (B) a graph quantifying fungal growth by calcofluor white staining and fluorometry of Af-dsRed coincubated with PX-12 and lethal and sublethal doses of $H_2O_2$; (C) images showing corneas of C57BL/6 mice infected with Af-dsRed at 24 hours, the mice at 0 and 6 hours after infection were treated with 3 mM PX-12 or vehicle topically applied to the infected mouse corneas; (D) a graph quantifying fungal dsRed expression after infection; and (E) a graph quantifying CFU after infection.

Figure 10:
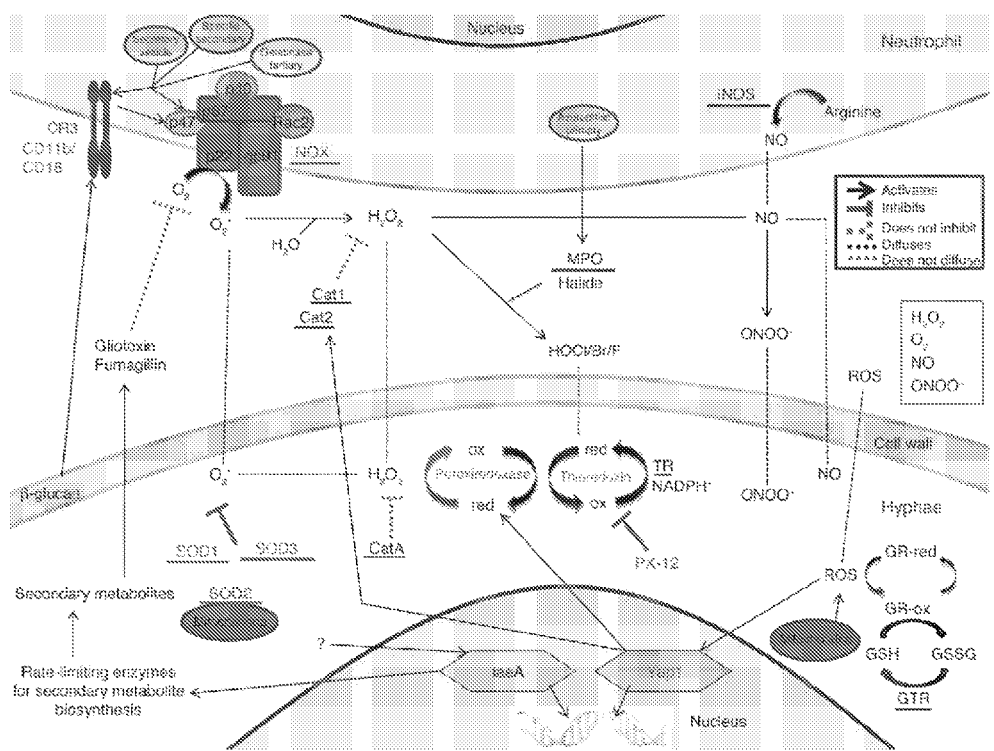

FIG. 10 is a schematic diagram showing oxidative stress responses at the neutrophil-hypha interface. Cat, catalase; GR, glutaredoxin; GSH, glutathione; GSSG, dimeric glutathione; GTR, glutathione reductase; HOCl, hypochlorous acid; ox, oxidized; red, reduced; TR, thioredoxin reductase.

DETAILED DESCRIPTION

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "thioredoxin protein inhibitor" refers to an agent, such as a small molecule, polypeptide, polynucleotide, that is capable of substantially reducing, inhibiting, blocking, and/or mitigating the activation of thioredoxin protein in a fungal cell. In some embodiments described herein, a thioredoxin protein inhibitor can bind to the active site of the thioredoxin protein, thereby inhibiting its ability to partake in redox reactions and quench cytoplasmic reactive oxygen species (ROS).

The term "fungal iron acquisition inhibitor" refers to an agent, such as a small molecule, polypeptide, or polynucleotide that is capable of substantially reducing, inhibiting, blocking, and/or mitigating the acquisition of iron in a fungal cell. In some aspects, a fungal iron acquisition inhibitor can include an agent that significantly increases host iron sequestration. In some aspects, a fungal iron acquisition inhibitor can include an agent that inhibits an iron acquisition mediator in a fungal cell. Exemplary fungal iron acquisition inhibitors can include iron chelators, siderophore biosynthesis inhibitors and siderophore binding proteins.

The term "Toll like receptor 4 antagonist" or "TLR4 antagonist" refers to an agent, such as a small molecule, polypeptide, polynucleotide, that is capable of substantially reducing, inhibiting, blocking, and/or mitigating the activation of TLR4 of a cell.

The term "subject" refers to any warm-blooded organism including, but not limited to, human beings, pigs, rats, mice, dogs, goats, sheep, horses, monkeys, apes, rabbits, cattle, etc.

The terms "treatment," "treating," or "treat" refers to any specific method or procedure used for the cure of, inhibition of, reduction of, elimination of, or the amelioration of a disease or pathological condition (e.g. fungal infection) including, for example, preventing fungal infection from developing, inhibiting fungal infection development, arresting development of clinical symptoms associated with fungal infection, and/or relieving the symptoms associated with fungal infection.

The term "effective amount" refers to a dosage of a thioredoxin protein inhibitor administered alone or in conjunction with any additional therapeutic agents that are effective and/or sufficient to provide treatment of fungal infection and/or a disease or disorder associated with fungal infection. The effective amount can vary depending on the subject, the disease being treated, and the treatment being effected.

The term "therapeutically effective amount" refers to that amount of a thioredoxin protein inhibitor administered alone and/or in combination with additional therapeutic agents that results in amelioration of symptoms associated with fungal infection and/or a disease or disorder associated with fungal infection and/or results in therapeutically relevant effect. By way of example, a "therapeutically effective amount" may be understood as an amount of thioredoxin protein inhibitor required to reduce fungal infection in a subject.

The terms "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

The term "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

The term "pharmaceutically acceptable salt" includes salts of compounds derived from the combination of the compound and an organic or inorganic acid or base. In some embodiments a pharmaceutically acceptable salt can include hydrohalide, acetate, sulfonate, tosylate, or a phosphate.

The term "unit dosage" formulations are those containing a dose or sub-dose of the administered ingredient adapted for a particular timed delivery. For example, "unit dosage" formulations are those containing a daily dose or unit or daily sub-dose or a weekly dose or unit or weekly sub-dose and the like.

The phrase "have the formula", "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups (e.g., an alkyl may optionally be substituted with one or more halogen atoms at any position along the alkyl chain), and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. In addition, the aforementioned functional groups may, if a particular group permits, be further substituted with one or more additional functional groups or with one or more hydrocarbyl moieties.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

The terms "optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Embodiments described herein relate to compositions and methods of treating a fungal infection, and particularly relates to compositions and methods of treating a fungal infection in a subject. In the methods described herein, the fungal infection can be treated, inhibited, and/or mitigated by administering an amount of a thioredoxin protein inhibitor to the fungal cells or the subject effective to block, inhibit, and/or mitigate thioredoxin protein activity in the fungal cells.

We have identified superoxide production by neutrophil NOX as the optimal effector for hyphal killing during fungal infection and have shown in the Example described herein that superoxide dismutase and thioredoxin are the key antioxidant agents used by hyphae during infection. We found that blocking the antioxidant activity of the fungus using a thioredoxin protein inhibitor can increase hyphal sensitivity to oxidative stress and decrease the threshold required for neutrophils to kill hyphae during infection. Accordingly, targeting fungal thioredoxin with a thioredoxin protein inhibitor can reduce fungal cell survival by inhibiting thioredoxin protein's ability to partake in redox reactions and quench cytoplasmic reactive oxygen species (ROS) and be used to treat fungal infections.

In some embodiments, a thioredoxin protein inhibitor for use in a method described herein can include any agent that when administered to a subject having a fungal infection is capable of binding to the active site of thioredoxin protein in a fungal cell and inhibits the protein's ability to partake in redox reactions and quench cytoplasmic ROS and thus inhibit the fungal cell's ability to minimize cellular damage from both exogenous and endogenous ROS sources.

In some embodiments, the thioredoxin protein inhibitor can be effective in the treatment of fungal infection by enhancing fungal cell susceptibility to killing by endogenous neutrophils of the subject. In other embodiments, a thioredoxin protein inhibitor is effective in killing fungal cells in a subject in the absence of neutrophils.

In some embodiments, the thioredoxin protein inhibitor can have a molecular weight of less than about 350 g/mole. In other embodiments, the thioredoxin protein inhibitor is a disulfide that has a molecular weight of less than about 350 g/mole, of less than about 300 g/mole, less than about 250 g/mole, or less than about 200 g/mole.

In some embodiments, the thioredoxin inhibitor can include an asymmetrical or symmetrical disulfide having a molecular weight less than about 350 g/mole and the formula $R_1$—S—S—$R_2$, wherein $R_1$ and $R_2$ are each selected from the group consisting of a substituted or unsubstituted alkyl, arylalkyl, imidazole, thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone; and pharmaceutically acceptable salts thereof.

In other embodiments, the thioredoxin protein inhibitor can include a asymmetrical or symmetrical disulfide having a molecular weight of less than about 350 g/mole and the formula $R_1$—S—S—Y—S—S—$R_2$, wherein $R_1$, $R_2$, and Y are each independently selected from the group consisting of a substituted or unsubstituted alkyl, arylalkyl, imidazole, thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone; and pharmaceutically acceptable salts thereof.

In some embodiments, Y can be selected from the group consisting of hydrogen, a substituted or unsubstituted alkyl, hydroxyalkyl, arylalkyl, and thiadiazoles. In other embodiments, $R_1$ and $R_2$ may each be selected form the group consisting of:

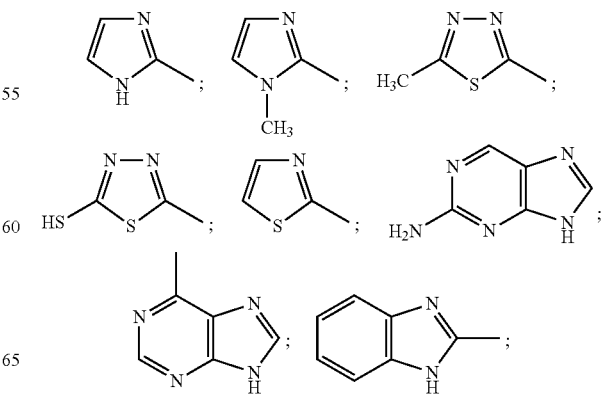

-continued

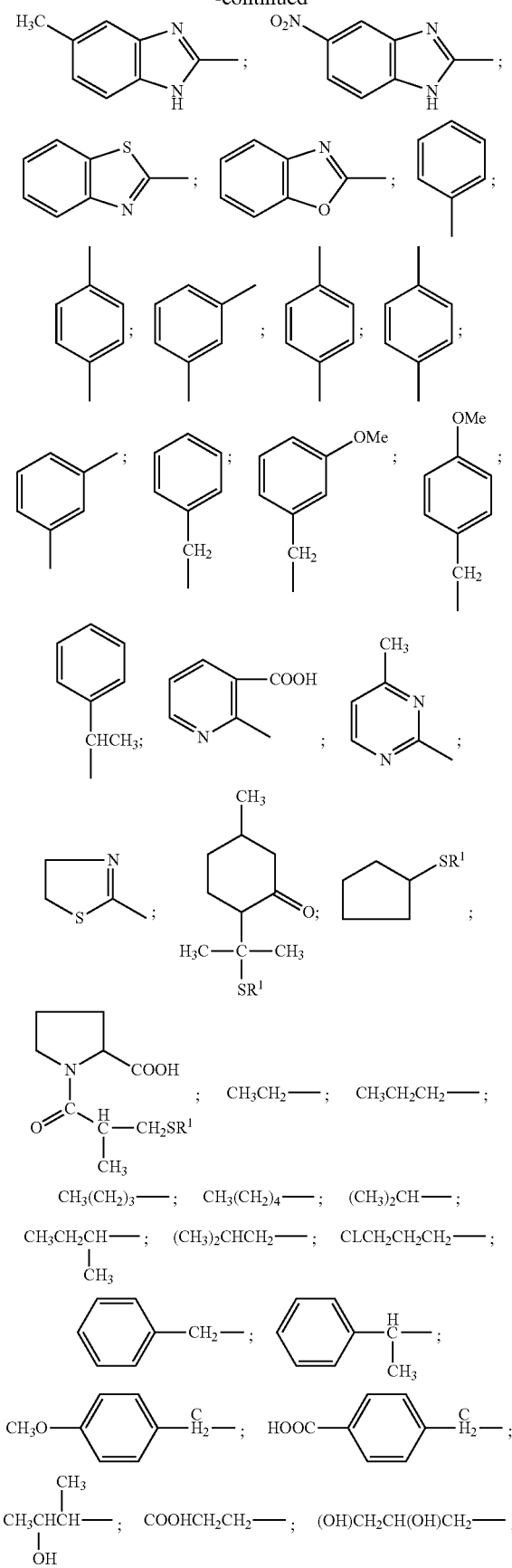

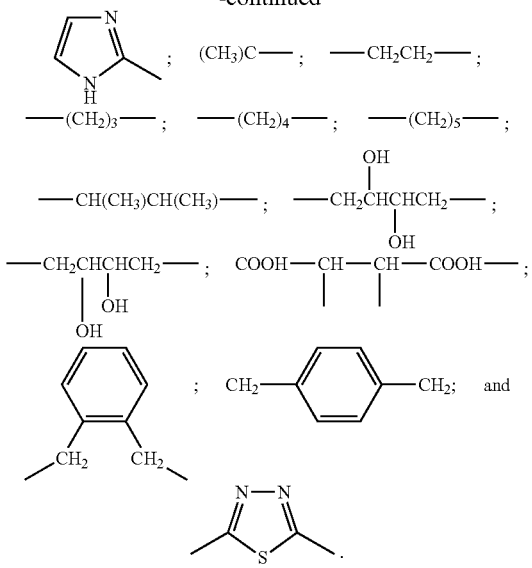

Examples of thioredoxin protein inhibitors that include an asymmetrical or a symmetrical disulfide having a molecular weight of less than about 350 g/mole and the formula $R_1-S-S-R_2$ or $R_1-S-S-Y-S-S-R_2$ are described in U.S. Pat. No. 6,552,060, which is herein incorporated by reference in its entirety.

In some embodiments, the thioredoxin protein inhibitor includes an asymmetric disulfide compound having the general formula (I):

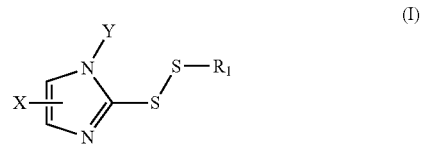

(I)

or a pharmaceutically acceptable salt thereof, wherein $R_1$ and Y are each independently selected from the group consisting of a hydrogen, a substituted or unsubstituted alkyl, arylalkyl, imidazole thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone. Generally, the X group is optional and when present may be any common functional group described herein including, but not limited to, hydrogen, alkyl, alkoxy, hydroxyl, carboxy, carbaldehyde, amino, halo, keto, nitro and combinations thereof. In some embodiments, $R_1$ is a branched alkyl group.

In other embodiments, the thioredoxin protein inhibitor is the small molecule PX-12 (1-methylpropyl 2-imidazolyl disulfide), having the structure:

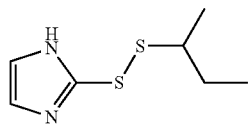

PX-12 or a pharmaceutically acceptable salt thereof.

A thioredoxin protein inhibitor used in methods described herein can also include a PX-12 analog and/or derivative thereof. Regardless of the thioredoxin protein inhibitor employed, the thioredoxin protein inhibitors can be administered to achieve at least transient blockade of thioredoxin protein function, thereby at least partially neutralizing or inhibiting the antioxidant effect of thioredoxin protein in fungal cells.

The subjects to which thioredoxin protein inhibitors are administered can include mammals afflicted with a fungal infection. In addition, subjects who do not have, but are at risk of developing a fungal infection can be treated according to the methods of the present invention. In such subjects, the treatment can inhibit or prevent the development of fungal infection in the subject.

For example, composition comprising the thioredoxin inhibitor described herein can be administered to neutropenic subjects. Neutropenic subjects can have neutropenia related to current or prior immunosuppressive therapy, an infection (e.g., AIDS) or an otherwise dysfunctional immune system. Neutropenic subjects are predisposed to the development of invasive fungal infections, most commonly including *Candida* species and *Aspergillus* species, and, on occasion, *Fusarium, Trichosporon* and *Dreschlera. Cryptoccocus* infection is also common in patients on immunosuppressive agents.

Non-limiting examples of fungal infections treated through a method include corneal, lung, skin/nail, mucosal, and systemic fungal infections.

In some embodiments, the compositions and methods described herein can be used to treat corneal fungal infections and related inflammation. For example, in certain embodiments, the methods may be used to treat fungal keratitis. Fungal keratitis treated may be related to fungal genera including, for example, *Fusarium, Penicillium, Aspergillus, Cephalosporium (Acremonium), Curvularia, Alternaria, Trichophyton, Microsporum, Epidermophyton, Scopulariopsis*, and *Candida*.

In particular embodiments, the methods described herein may be used to treat: lung fungal infections related to fungal genera including for example, *Aspergillus* and *Histoplasma*; skin/nail fungal infections (e.g., Athlete's Foot) related to fungal general including for example, *Microsporum, Epidermophyton* and *Trichophyton*; mucosal fungal infections related to fungal genera including for example, *Candida*; and systemic fungal infections related to fungal genera including for example, *Candida* and *Aspergillus.*

Methods described herein may also be used in the treatment and prevention of a nosocomial fungal infection (i.e., hospital-acquired fungal infections). In some embodiments, a thioredoxin protein inhibitor can be administered to a subject who has undergone a medical intervention (e.g., a surgical intervention). In an alternative embodiment, a thioredoxin protein inhibitor can be administered to a subject prior to the subject undergoing a medical intervention. Additionally, a thioredoxin protein inhibitor can be administered to a subject both prior to and after the subject has undergone a medical intervention.

The thioredoxin protein inhibitor used in methods of described herein can be administered to the subject to treat fungal infection using standard methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the methods described herein can be altered, stopped, or re-initiated in a subject depending on the status of fungal infection (e.g., corneal fungal infection). Treatment can be carried out as intervals determined to be appropriate by those skilled in the art. For example, the administration can be carried out 1, 2, 3, or 4 times a day. In another aspect of the present invention, a thioredoxin protein inhibitor can be administered after induction of the inflammatory response/exposure to human neutrophils has occurred.

The methods described herein include administering to the subject a therapeutically effective amount of a thioredoxin protein inhibitor. Determination of a therapeutically effective amount is within the capability of those skilled in the art. The exact formulation, route of administration, and dosage can be chosen by the individual physician in view of the subject's condition.

Formulation of pharmaceutical compounds for use in the modes of administration noted above (and others) are described, for example, in *Remington's Pharmaceutical Sciences* ($18^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In some embodiments, the thioredoxin protein inhibitor can be provided in ophthalmic preparation that can be administered to the subject's eye for the treatment of a corneal fungal infection. The ophthalmic preparation can contain a thioredoxin protein inhibitor in a pharmaceutically acceptable solution, suspension, or ointment. Some variations in concentration can occur, depending on the particular thioredoxin protein inhibitor employed, the condition of the subject to be treated and the like, and the person responsible for treatment can determine the most suitable concentration for the individual subject. In one particular embodiment, an ophthalmic preparation for the treatment of a corneal fungal infection includes the thioredoxin protein inhibitor PX-12 at a concentration of 3 mM (0.056% (w/w)). The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The thioredoxin protein inhibitors can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin include, for example, ointments, creams, gels and pastes comprising the thioredoxin protein inhibitor in a pharmaceutical acceptable carrier. The formulation of thioredoxin protein inhibitors for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with corneal fungal infection (or at risk of corneal fungal infection) which are not readily accessible or suitable for ophthalmic (e.g. eye-drops) and/or topical administration, can be treated by a systemic approach, such as intravenous infusion. For example, the thioredoxin protein inhibitor can be administered at a low dosage by continuous intravenous infusion. In another example, in which a patient requires longer-term care, the thioredoxin protein inhibitor can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the thioredoxin protein inhibitor to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the thioredoxin protein inhibitor.

In other embodiments, the thioredoxin protein inhibitor can be provided, applied, coated, and/or administered to a medical device to prevent, inhibit, mitigate, and/or treat fungal infection associated with use of the device. Coatings including thioredoxin protein inhibitors can be applied to a number of medical device materials known in the art in order to coat medical/surgical devices and permanent medical/surgical implants. A coating including a thioredoxin protein inhibitor described herein can be provided on at least a portion of the medical device.

In some embodiments, the medical device provided or coated with the thioredoxin inhibitor can include percutaneous devices, such as catheters, and implanted medical devices, including, but not limited to, pacemakers, vascular grafts, stents, and heart valves, that commonly serve as foci for bacterial infection. The tendency of some microorganisms (e.g., *Candida*) to adhere to and colonize the surface of the device, promotes such infections, which increase the morbidity and mortality associated with use of the devices. Therefore, in some embodiments, a thioredoxin protein inhibitor or pharmaceutical compositions thereof can be used to treat or prevent fungal infection on a medical device by contacting the device with a thioredoxin protein inhibitor or pharmaceutical composition thereof in an amount effective to treat fungal infection or inhibit fungal growth when implanted in a subject. For example, in certain embodiments, the coating can include an amount of a thioredoxin protein inhibitor effective to treat fungal infection or inhibit fungal growth related to *Candida* when implanted in a subject.

It will be appreciated, a medical device as described herein can include any instrument, implement, machine, contrivance, implant, or other similar or related article, including a component or part, or accessory which is: recognized in the official U.S. National Formulary the U.S. Pharmacopoeia, or any supplement thereof; intended for use in the diagnosis of disease or other conditions, or in the cure, mitigation, treatment, or prevention of disease, in humans or in other animals; or, intended to affect the structure or any function of the body of humans or other animals, and which does not achieve any of its primary intended purposes through chemical action within or on the body of human or other animal, and which is not dependent upon being metabolized for the achievement of any of its primary intended purposes.

A medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, penile implants, vascular implants and grafts, intravenous catheters, small diameter grafts, surgical mesh, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

The medical device may additionally include either arterial or venous pacemakers, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/

IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, bandages, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, and cardiac valves.

The medical device can include any material known in the art including, for example, biocompatible polymers, such as PTFE, ePTFE, poly(ethylene co-vinyl alcohol) (pEVOH) and silicone, metals and metal alloys, such as gold, NITINOL, NiTi and titanium, and glass. Other examples of suitable biocompatible polymers can include polyalkylene oxides, polymethacrylates, polyurethanes, cellulosics, polyhydroxyalkyl acrylates, polyesters, and polymers comprised of at least one polyethylene monomer, such as polyethylene glycol (PEG) or polyethylene oxide, polymers comprised of polyamine monomers, such as polyethyleneimine (PEI), and poly(L-lactide) (PLLA), poly-p-dioxanone (PDO), polycaprolactone (PCL), polyvinyl alcohol (PVA), and poly(lactide-co-glycolide) (PLG).

Other embodiments described herein relate to a contact lens for treating corneal fungal infection in a subject. The contact lens includes a contact lens substrate and a coating provided on at least a portion of the substrate. The coating can include an amount of thioredoxin protein inhibitor effective to treat, inhibit, and/or prevent fungal infection in a subject upon administration of the contact lens to the subject.

Coatings including thioredoxin protein inhibitors can be applied to a number of contact lens substrate materials known in the art. Virtually any substrate known in the art, which can be fashioned into a contact lens, can be used with the thioredoxin inhibitors described herein provided the substrate is optically transparent.

In some embodiments, the substrate can include optically transparent materials that allow oxygen to reach the cornea in an amount, which is sufficient for long-term corneal health. Examples of substrates include polymers made from hydrophobic materials, such as silicone copolymers, interpolymers, oligomers, and macromers. Illustrative polysilicones are polydimethyl siloxane, polydimethyl-co-vinylmethylsiloxane. Other silicones include silicone rubbers described in U.S. Pat. No. 3,228,741 to Becker; blends such as those described in U.S. Pat. No. 3,341,490 to Burdick et al., and silicone compositions such as described in U.S. Pat. No. 3,518,324 to Polmanteer. Substrates described in U.S. Pat. Nos. 4,136,250; 5,387,623; 5,760,100; 5,789,461; 5,776,999; 5,849,811; 5,314,960 and 5,244,981 can also be used in the invention. Cross-linked polymers of propoxylate of methyl glucose and propylene oxide and HEMA-based hydrogels can also be used as substrates of the contact lens.

Examples of silicone compositions that can be used in forming the contact lens are the cross-linked polysiloxanes obtained by cross-linking siloxane prepolymers by means of hydrosilylation, co-condensation and by free radical mechanisms such those described by Chen in U.S. Pat. No. 4,143,949, which is incorporated herein by reference. Additional examples of silicone-based substrates are cross-linked polymers of α,ω-bisamionpropyl polydimethylsiloxane, and gylycidyl methacrylate, cross-linked polymers. Examples of other silicone compositions also contemplated are made from combining a methacrylate with one or more silicone monomers in the presence of a group transfer polymerization (GTP) catalyst to form a macromer that is subsequently polymerized with other monomers to give the final substrate. Initiators, reaction conditions, monomers, and catalysts that can be used to make group transfer (GTP) polymers are described in "Group Transfer Polymerization" by O. W. Webster, in Encyclopedia of Polymer Science and Engineering Ed. (John Wiley & Sons) p. 580, 1987. Substrates described in U.S. Pat. No. 6,951,894 are also suitable for use in the present invention.

The coating including the thioredoxin inhibitor can be prepared and applied as an aqueous solution, suspension, or colloid and then applied to the contact lens substrate according to any process that can provide the coating in contact with the substrate. For example, processes for applying the coating to the substrate include immersion, spraying, brushing, and spin coating. Once the lens substrate is coated it may be subjected to any number of additional steps that are conducted in the manufacture of contact lenses. These can include, for example, swelling and washing steps, the addition of additives such as surfactants, extraction steps and the like.

The coating including the thioredoxin protein inhibitor can adhere to the contact lens by, for example, chemical bonding, such as covalent or ionic bonding, or physical bonding. In some aspects, the coating can remain affixed to the lens substrate throughout its useful life (e.g., storage time plus the time in which it will be in contact with a user's eye).

The contact lens can also include more than one layer of coating. This can be desirable where the coating layer will provide the requisite surface properties (e.g. treatment of corneal fungal infection) but is not particularly compatible with the lens substrate itself. For example, a tie-layer or coupling agent can be used to adhere the coating to the substrate. Selections of compatible lens substrate, thioredoxin protein inhibitor coating, and tie-layer (if necessary) materials is well within the knowledge of one skilled in the art.

In some embodiments, the contact lens is non-toxic to the subject's cornea and other tissue while providing for the treatment of corneal fungal infection in the subject.

Other embodiments described herein relate to an ophthalmic solution for treating corneal fungal infection in a subject. The solution can be aqueous and include a thioredoxin protein inhibitor as described above. Examples of solutions useful that can be used in the treatment of corneal fungal infection and related inflammation include solutions that are contacted with eye lids and/or eyes, such as multipurpose lens solutions, ophthalmalic rinse solutions, surgical scrubs for eye use, eye drops, eye wash solutions, contact lens solutions, topical over the counter ocular and periocular solutions (i.e. artificial tears), ocular and periocular cleaning solutions, eye irrigating solutions, and/or antibacterial solutions for surgical scrubs or topical application.

In some aspects, a thioredoxin protein inhibitor may be added to a commercially available contact lens solution or a multipurpose lens solution to treat corneal fungal infection. In other aspects, a thioredoxin protein inhibitor may be added to an aqueous solution prepared for use as a contact lens or multipurpose lens solution that is not commercially available to treat corneal fungal infection.

In some aspects where the ophthalmic solution includes a cleaning solution, the cleaning solution can include cleaning agents to effectively clean a lens of film deposits and surface debris. Examples of cleaning agents that can be used include, poloxamers and tetronic surfactants comprising poly(oxythylene) hydrophilic units. In all embodiments, the cleaning agents are nontoxic, and do not distort the vision of the subject being treated for corneal fungal infection.

In other aspects, thioredoxin protein inhibitors may be added to tonicity agents and buffers that are found in conventional ophthalmic solutions. Examples of tonicifiers include dextrose, potassium chloride and/or sodium chloride. Examples of buffers include boric acid, sodium borate, sodium or potassium citrate, sodium bicarbonate, sodium phosphate, and potassium phosphate.

Additionally, antibacterial agents found in conventional ophthalmic solutions, such as multipurpose lens solutions, may be added. Antibacterial agents for use in the solution include, for example, polyaminopropyl biguanide, alexidine hydrochloride, polyquaternium-1, polyquaternium 42, myristamidopropyl dimethylamine, or other agents known to those skilled in the art.

In some aspects, the solution may further include a comfort or moisturizing agent to provide hydration and lubrication of a subject's contact lens. Such agents include, for example, polyquaternium 10, poloxamer, propylene glycol, hydroxypropylmethylcellulose (HPMC), or other agents known to those skilled in the art.

Since, in some aspects, the solution is intended to be administered topically to the eyelids and/or eye, it is contemplated that the solution be free of pathogenic organisms and/or sterile. A benefit of a sterile solution is that it reduces the possibility of introducing contaminants into a subject's eyelids and/or eye. Sterility or adequate antimicrobial preservation may be provided as part of the present solutions of the present invention. In some aspects, the solutions are produced under sterile conditions.

In addition to or in place of sterilization, aqueous solutions of the thioredoxin protein inhibitor may contain a physiologically acceptable preservative to minimize the possibility of microbial contamination. A physiologically acceptable preservative may be used in the solutions of the present invention to increase the stability of the solutions. Preservatives include, for example, polyaminopropyl biguanide, polyhexamethylene biguanide (PHMB), polyquaternium-1, myristamidopropyl, and sorbic acid.

In yet another embodiment, the thioredoxin protein inhibitors and methods of their use described herein can be administered or applied to a device as part of a combinatorial therapy with additional therapeutic agents. The phrase "combinatorial therapy" or "combination therapy" embraces the administration of a thioredoxin protein inhibitor, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

For example, the combinational therapy can include the administration of a thioredoxin protein inhibitor with at least one antibacterial, antiviral or antifungal agent to treat a microbial infection and related inflammation (e.g., corneal inflammation) in a subject. Antibiotic agents administered in conjunction with a thioredoxin protein inhibitor or pharmaceutical composition can include, but are not limited to aminosalicylic acid, nalidixic acid, amoxicillin, amoxicillin and potassium clavulanate, ampicillin, ampicillin and sulbactam, azithromycin, bacampicillin, carbenicillin indanyl sodium (and other carbenicillin salts), capreomycin, cefadroxil, cefazolin, cephalexin, cephalothin, cephapirin, cephaclor, cefprozil, cephadrine, cefamandole, cefonicid, ceforanide, cefuroxime, cefixime, cefoperazone, cefotaxime, cefpodoxime, ceftazidime, ceftibuten, ceftizoxime, ceftriaxone, cefepime, cefmetazole, cefotetan, cefoxitin, ciprofloxacin, clarithromycin, clindamycin, clofazimine, cloxacillin, co-trimoxazole, cycloserine, dicloxacillin, dirithromycin, erythromycin (and erythromycin salts such as estolate, ethylsuccinate, gluceptate, lactobionate, stearate), ethambutol-HCl and other salts, ethionamide, fosfomycin, gentamycin (fortified with vancomycin for methicillin-resistant *Staphylococcus aureus* (MRSA) infections) imipenem, isoniazid, levofloxacin, lomefloxacin, loracarbef, methicillin, methenamine, metronidazole, mezlocillin, nafcillin, nitrofurantoin, norfloxacin, novobiocin, ofloxacin, oxacillin, penicillin V, penicillin salts, penicillin complexes, pentamidine, piperacillin, piperacillin and tazobactam, sparfloxacin, sulfacytine, sulfamerazine, sulfamethazine, sulfamethizole, sulfasalazine, sulfisoxazole, sulfapyrazine, sulfadiazine, sulfinethoxazole, sulfapyridine, ticarcillin, ticarcillin and potassium clavulanate, trimethoprim, trimetrexate, troleandomycin, $4^{th}$ generation fluroquinoline like moxifloxacin or gatifloxacin, cefazolin or vancomycin and fluoroquinolone vancomycin and mixtures thereof.

In one specific example, the combinational therapy includes a thioredoxin protein inhibitor and at least one ophthalmic antibiotic or ophthalmic antiviral. Ophthalmic antibiotics include, for example, chloramphenicol sodium succinate ophthalmic (chloramphenical); CORTISPORIN (neomycin and polymyxin β sulfates and hydrocortisone acetate cream); ILOTYCIN (erythromycin ophthalmic ointment); NEODECADRON (neomycin sulfate-dexamethasone sodium phosphate); POLYTRIM (trimethoprim and polythyxin β sulfate opthalmic solution); TERRA-CORTRIL (oxytetracycline HCL and hydrocortisone acetate); TERRAMYCIN (oxytetratcycline); and TOBRADEX (tobramycin and dexamethosone ophthalmic suspension and ointment).

Ophthalmic antivirals include, for example, VIRA-A ophthalmic ointment, (vidarabine). Opthalmic quinalones include, for example, CHIBROXIN (norfloxacin ophthalmic solution); CILOXAN ophthalmic solution, (Ciprofloxacin HCL); and Ocuflox ophthalmic solution (ofloxacin). Opthalmic sulfonamides include, for example, BLEPHAMIDE ophthalmic ointment (sulfacetamide sodium and prednisolone acetate); and BLEPHAMIDE ophthalmic suspension (sulfacetamide sodium and prednisolone acetate).

Additionally, a thioredoxin protein inhibitor may be administered to a subject for the treatment of a fungal infection in combination with one or more other antifungal agents, such as a polyenic derivative (e.g. Amphotericin B, Nystatin, a lipid formulation of Amphotericin B, filipin and/or pimaricin (Natamycin)), 5-fluctyosine, an azole derivative (e.g., Voriconazole Fluconazole, Intraconazole, Ketoconazole, Miconazole, Clotrimazole, ZD-08070, UK-109496, SCH 56592), 5 Fluorocytosine, a Pneumocandin or Echinocandin derivative such as Cilofungin, LY-303366, L 733560, or L-743872. In an exemplary embodiment, an ophthalmic preparation administered to a subject for the treatment of a corneal fungal infection and related inflammation includes the thioredoxin protein inhibitor PX-12 (0.056% (w/w)) with natamycin (5% (w/w)), voriconazole (1% w/w) and/or amphotericin B (0.3% (w/w)).

In still other embodiments, the thioredoxin protein inhibitor may be administered to a subject for the treatment of a fungal infection in combination with a spleen tyrosine kinase inhibitor (Syk inhibitor). Examples of Syk inhibitors include fostamatinib (r-406) (Tamatinib fosdium; R-788; NSC-745942; R-935788), and PRT062607, a novel oral spleen tyrosine kinase (SYK) inhibitor.

In other embodiments, the thioredoxin protein inhibitor may be administered to a subject for the treatment of a fungal infection in combination with a fungal iron acquisition inhibitor. A fungal iron acquisition inhibitor can include any agent that when topically or locally administered to a subject having a fungal infection is capable of substantially reducing, inhibiting, blocking, and/or mitigating the acquisition of iron in a fungal cell and thus inhibit the fungal cell's ability to minimize cellular damage from both exogenous and endogenous reactive oxygen species (ROS) sources and reduce the fungal cell's growth rate. In certain embodiments, a fungal iron acquisition inhibitor employed in the method described herein is effective in the treatment of fungal infection by enhancing fungal cell susceptibility to endogenous neutrophils induced fungal cell death. In other embodiments, a fungal iron acquisition inhibitor is effective in killing and/or reducing the growth rate of fungal cells in a subject in the absence of neutrophils.

In certain embodiments, the fungal iron acquisition inhibitor can include an agent capable of inhibiting the ability of fungal cells to acquire iron in a subject by sequestering host free (or bio-available) iron from the fungal cell microenvironment. In some embodiments an agent that sequesters host free iron can be an iron chelator. As used herein, the term "iron chelator", or "iron chelating compound", refers to a compound that binds iron between two or more separate binding sites so as to form a chelate ring or rings. An iron chelating compound bound or complexed with iron is referred to herein as an iron chelate.

An iron chelating compound can be bidentate (or didentate), which binds iron using two separate binding sites. Iron chelating compounds of the invention also can be tridentate, tetradentate or higher order multidentate iron chelation compounds binding iron with three, four or more separate binding sites, respectively. Iron chelating compounds can include chelation compounds that can bind to all oxidation states of iron including, for example, iron (−II) state, iron (−I) state, iron (0) state, iron (I) state, iron (II) state (ferrous), iron (III) state (ferric), iron (IV) state (ferryl) and/or iron (V). Iron chelation therapy refers to the use of an iron chelator to bind with iron in vivo to form an iron chelate so that the iron loses its toxic effect or adverse physiological activity. Alternatively, chelated iron becomes unavailable to the infectious organism.

One example of an iron chelator that can be used as a fungal iron acquisition inhibitor in the methods described herein can include the iron chelating protein lactoferrin. In an exemplary embodiment, an $A.\ fumigatus$ infected cornea can be treated by topically administering lactoferrin (e.g., at 10.4 µg in 8 µl) post infection in combination with the thioredoxin inhibitor to significantly decrease fungal mass and compared to untreated infected corneas.

Another example of an iron chelator that can be used in combination with the thioredoxin inhibitor in the methods described herein can include a 3,5-diphenyl-1,2,4-triazole derivative or a salt thereof, e.g., deferasirox, deferiprone, deferitrin, L1NAU, and deferoxamine. In certain embodiments, the iron chelator can be deferiprone. The term "deferiprone," as it is used herein is intended to mean an iron chelating compound having the structure 1,2 dimethyl-3-hydroxypyrid-4-1. Deferiprone (Def) also is known in the art as L1, CP20, Ferriprox, or Kelfer. Deferiprone is a member of the α-ketohydroxypyridine class of iron chelators and is commercially available from, for example, Apotex, Inc. (Weston, Ontario, Canada).

Other iron chelating compounds can also be used as a fungal iron acquisition inhibitor in the methods described herein. Such other iron chelating compounds can include naturally occurring siderophores and xenosiderophores as well as non-naturally occurring siderophores and xenosiderophores.

The term "siderophore," as it is used herein is intended to mean an iron chelator that facilitates iron gathering by an organism. For example, under conditions of iron starvation, many fungi synthesize siderophores that function in iron gathering through iron binding and uptake. Siderophores are generally low molecular weight compounds (e.g., less than about 2,000 MW) and can exhibit either or both cellular uptake and/or iron storage functions. Siderophores are synthesized by the utilizing organism. As compared to the term "iron chelator," which is generally used without reference to organism or species specificity, the term "siderophore" as it is used herein refers to an iron chelator in context with, or relative to, the siderophore-producing and utilizing organism or species. Accordingly, although iron chelating siderophores bind and decrease iron levels from the extracellular environment, because they facilitate iron uptake and use by a pathogen they have diminished therapeutic value when used for iron chelation therapy targeting a condition caused by the siderophore-producing organism.

The term "xenosiderophore," as it is used herein is intended to mean a siderophore not produced by the utilizing fungus or organism. The term "xenosiderophore" refers to an iron chelator in context with, or relative to, the xenosiderophore utilizing organism or species. Similar to siderophores, xenosiderophores exhibit therapeutic value when used for iron chelation therapy that targets a condition caused by a non-utilizing organism. Siderophore and xenosiderophore synthesis and use can be found described in, for example, Howard, D. H., FEMS Immunology and Medical Microbiology 40:95-100 (2004).

Examples of siderophores and xenosiderophores include hydroxamates and polycarboxylates. Hydroxamates contain an N-δ-hydroxyomithine moiety and are generally categorized into four exemplary families One category includes rhodotorulic acid, which is the diketopiperazine of N-δ-acetyl-L-N-δ-hydroxyomithine. Included within this category are derivatives such as dihydroxamate named dimerum acid. A second category includes the coprogens, which contain an N-δ-acyl-N-δ-hydroxy-L-ornithine moiety. Coprogens also can be considered trihydroxamate derivatives of rhodotorulic acid with a linear structure. A third category includes the ferrichromes, which consist of cyclic peptides containing a tripeptide of N-δ-acyl-N-δ-hydroxyornithine and combinations of glycine, serine or alanine. The fourth exemplary category includes the fusarinines, also called fusigens, which can be either linear or cyclic hydroxamates. Fusarinine is a compound characterized by N acylation of N-hydroxyornithine by anhydromevalonic acid.

Polycarboxylates consist of a citric acid-containing polycarboxylate called rhizoferrin. The molecule contains two citric acid units linked to diaminobutane. Rhizoferrin is widely distributed among the members of the phylum Zygomycota, having been observed in the order Mucorales and in the order Entomophthorales. Other categories of siderophores useful as iron chelating compounds in a method of the invention include, for example, the phenolate-catecholate class of siderophores, hernin, and β-ketoaldehyde phytotoxins.

In other embodiments, the fungal iron acquisition inhibitor administered or used in combination with the thioredoxin inhibitor can be an agent capable of inhibiting the fungal siderophore biosynthesis of a pathogenic fungal cell in a subject (i.e., a fungal siderophore biosynthesis inhibitor). Pathogenic fungal siderophore biosynthesis has been identified as an essential mediator of fungal growth during infection. For example, siderophore production by filamentous fungi requires the precursor amino acid ornithine which is produced in the mitochondria and exported to the cytoplasm through the ornithine transporter AMcA or produced directly in the cytosol from arginine by the enzyme arginase. It is contemplated that agents capable of targeting fungal arginase (i.e., arginase inhibitors), which mediates ornithine and therefore siderophore biosynthesis, can be used as fungal iron acquisition inhibitors in a method described herein by facilitating neutrophil killing of fungal cells and inhibiting fungal growth during infection.

In an exemplary embodiment, A. fumigatus infected mice treated with the arginase inhibitor, (S)-(2-Boronoethyl)-L-cysteine (BEC), (e.g., 40 μg in 8 μl) in combination with a thioredoxin inhibitor had significantly lower fungal mass to control infected mice. Furthermore, it was shown that there were no apparent ill effects on the cornea following BEC treatment.

Additional arginase inhibitors can include but are not limited to 2(S)-amino-6-boronohexanoic acid (ABH), $N^G$-Hydroxy-L-arginine (NOHA), $N^\omega$-Hydroxy-nor-L-arginine (nor-NOHA) and DL-alpfa-Difluoromethylornithine (DFMO also called eflornithine).

In other embodiments, a fungal siderophore biosynthesis inhibitor can include a statin drug. Satins target the enzyme HMG-CoA reductase, which is required for fungal siderophore biosynthesis. As used herein, the term "statin" or "statin drug" can refer to any compound or agent capable of substantially inhibiting HMG Co-A (3-hydroxy methylglutaryl coenzyme A) reductase.

Statins that can be used for administration, or co-administration with the thioredoxin inhibitors described herein include, but are not limited to, simvastatin (U.S. Pat. No. 4,444,784), mevistatin, lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. No. 5,622,985, U.S. Pat. No. 5,135,935, U.S. Pat. No. 5,356,896, U.S. Pat. No. 4,920,109, U.S. Pat. No. 5,286,895, U.S. Pat. No. 5,262,435, U.S. Pat. No. 5,260,332, U.S. Pat. No. 5,317,031, U.S. Pat. No. 5,283,256, U.S. Pat. No. 5,256,689, U.S. Pat. No. 5,182,298, U.S. Pat. No. 5,369,125, U.S. Pat. No. 5,302,604, U.S. Pat. No. 5,166,171, U.S. Pat. No. 5,202,327, U.S. Pat. No. 5,276,021, U.S. Pat. No. 5,196,440, U.S. Pat. No. 5,091,386, U.S. Pat. No. 5,091,378, U.S. Pat. No. 4,904,646, U.S. Pat. No. 5,385,932, U.S. Pat. No. 5,250,435, U.S. Pat. No. 5,132,312, U.S. Pat. No. 5,130,306, U.S. Pat. No. 5,116,870, U.S. Pat. No. 5,112,857, U.S. Pat. No. 5,102,911, U.S. Pat. No. 5,098,931, U.S. Pat. No. 5,081,136, U.S. Pat. No. 5,025,000, U.S. Pat. No. 5,021,453, U.S. Pat. No. 5,017,716, U.S. Pat. No. 5,001,144, U.S. Pat. No. 5,001,128, U.S. Pat. No. 4,997,837, U.S. Pat. No. 4,996,234, U.S. Pat. No. 4,994,494, U.S. Pat. No. 4,992,429, U.S. Pat. No. 4,970,231, U.S. Pat. No. 4,968,693, U.S. Pat. No. 4,963,538, U.S. Pat. No. 4,957,940, U.S. Pat. No. 4,950,675, U.S. Pat. No. 4,946,864, U.S. Pat. No. 4,946,860 U.S. Pat. No. 4,940,800, U.S. Pat. No. 4,940,727, U.S. Pat. No. 4,939,143, U.S. Pat. No. 4,929,620, U.S. Pat. No. 4,923,861, U.S. Pat. No. 4,906,657, U.S. Pat. No. 4,906,624 and U.S. Pat. No. 4,897,402, the disclosures of which patents are incorporated herein by reference.

In other embodiments, a fungal iron acquisition inhibitor can include a siderophore-binding agent. A siderophore-binding agent described herein can include any agent (e.g., a protein) that is capable of binding to a pathogenic fungal siderophore and substantially reducing, inhibiting, blocking, and/or mitigating the functional activity of the pathogenic fungal siderophore. An example of a siderophore-binding protein is lipocalin-1 (Lcn-1). Lcn-1 is produced by humans and binds to a wide range of bacterial and fungal hydroxymate-type siderophores. Therefore, a fungal siderophore binding protein for use in a method described herein can include Lcn-1.

The invention is further illustrated by the following example, which is not intended to limit the scope of the claims.

Example

In this Example, we examined the role of ROS in killing Aspergillus and Fusarium hyphae by human neutrophils and in a murine model of fungal keratitis. We show that hyphae activate neutrophil NOX through CD18 and that NOX activation is essential for killing hyphae. In addition, utilizing mutant A. fumigates strains, we show that the ROS-sensing transcription factor Yap1, the ROS-detoxifying enzyme superoxide dismutase, and the Yap1-regulated thioredoxin antioxidant pathway, but not catalases or fungal secondary metabolites such as gliotoxin are required for resistance to oxidation by neutrophils. Last, using pharmacologic inhibitors of thioredoxin, we provide proof of concept that targeting fungal anti-oxidative stress responses can enhance fungal clearance from infected tissues and may represent a new avenue for treatment of fungal infections.

Methods

Source of Mice

C57BL/6 mice (6-12 weeks old) and $Cybb^{-/-}$ mice were purchased from The Jackson Laboratory. $Cd18^{-/-}$ mice were provided by Claire Doerschuk (University of North Carolina, Chapel Hill, N.C., USA), and $Cxcr2^{-/-}$ mice were provided by Richard Ransohoff (Cleveland Clinic, Cleveland, Ohio, USA). $Dectin-1^{-/-}$ mice were provided by Yoichiro Iwakura (Tokyo University, Tokyo, Japan). All mice used in this study were on a C57BL/6 background.

Fungal Strains, Media, and Growth Conditions

Table 1 lists the genotype and phenotype of all strains utilized in this study. A. fumigatus and A. flavus strains used in this study were cultured on Vogel's minimal medium (VMM) with or without 2% agar unless otherwise stated. *F. oxysporum* and *F. solani* strains were cultured on Sabouraud dextrose medium. To visualize fungi in the transparent murine cornea, we utilized fluorescent strains of *Aspergillus* or *Fusarium* species expressing either RFP or GFP. Af-dsRed constitutively expresses enhanced monomeric dsRed protein (gpdA promotor driven; pyrG1 selection marker). The strain *A. flavus* 70-GFP constitutively expresses GFP (gpdA promotor driven; niaD selection marker; provided by Rajah Rajasekaran, USDA, New Orleans, La., USA). The strains FoxL-RFP and FoxL-GFP are *F. oxysporum lycopersici* strains constitutively expressing either RFP or GFP, which were provided by Seogchan Kang (Pennsylvania State University, University Park, Pa., USA). The *A. fumigatus* strain Af-BP was isolated from a keratitis patient at Bascom Palmer Eye Institute and provided by Darlene Miller (University of Miami, Miami, Fla., USA). The *A. flavus* strain TN-302 was isolated from a keratitis patient at Aravind Eye Hospital, Tamil Nadu, India, and provided by Lalitha Prajna. The *F. oxysporum* strain 8996 was isolated from a keratitis patient at the Cole Eye Institute, Cleveland Clinic. For our studies on gliotoxin, June Kwon-Chung (NIAID, Bethesda, Md., USA) provided *A. fumigatus* strains B-5233 (WT), ΔgliP, and gliPR. Additionally, Nancy Keller (University of Wisconsin, Madison, Wis., USA) provided the *A. fumigatus* strains Af293 (WT), ΔgliZ, gliZR, ΔlaeA, laeA-R, as well as the *Aspergillus flavus* strains *A. flavus* NRRL3357 (WT), ΔlaeA, and laeA-R. For ROS scavenging studies, we used *A. fumigatus* strains G10 (WT), ΔcatA, and Δcat1/2, and Ku80 (WT), Δsod1/2/3, and Dal (WT), Δyap1 (36-38).

*Aspergillus* strains were cultured for 2-3 days on VMM in 25-cm2 tissue culture flasks. Fresh conidia were disrupted with a bacterial L-loop, harvested in 5 ml PBS, and filtered through sterile, PBS-soaked cotton gauze in a 10-ml syringe to obtain pure conidial suspensions. Conidia were quantified using a hemocytometer and adjusted in PBS to a final stock solution: *A. fumigatus*, 20,000 conidia/µl; *A. flavus*, 20,000 conidia/µl; *F. oxysporum*, 25,000 conidia/µl. Subsequently, mice were anesthetized with 1.25% 2,2,2-tribromoethanol. The corneal epithelium of anesthetized mice was abraded using a 30-gauge needle, through which a 2-µl injection containing conidia was released into the corneal stroma using a 33-gauge Hamilton syringe (total: *A. fumigatus*, 40,000 conidia; *A. flavus*, 40,000; *F. oxysporum*, 50,000). Mice were examined daily under a stereomicroscope for corneal opacification, ulceration, perforation, and fungal fluorescent protein expression. At set time points, animals were euthanized by $CO_2$ asphyxiation, and eyes were either placed in 10% formalin and embedded in paraffin and sectioned at 5-µm intervals or excised and placed in 1 ml sterile saline and homogenized for quantitative culture. For depletion of neutrophils in mice, 400 µg of anti-mouse neutrophil antibody (NIMP-R14) was injected at day 1 prior to infection. To detect ROS production in the mouse cornea during fungal infection, 2 µl of 12.5-ng/ml CFDA (Invitrogen) was injected into the stroma of anesthetized mice and eyes imaged under standard GFP filters after 10 minutes incubation at 25° C. Subsequently, mice were euthanized, and eyes processed accordingly. To inhibit RNS production during corneal infection, 500 µg of the irreversible iNOS inhibitor 1400 W was injected i.p. into C57BL/6 mice at 6,

TABLE 1

Fungal strains utilized in this study

| Strain | Genotype | Phenotype |
|---|---|---|
| *A. fumigatus* | | |
| Af-BP | Keratitis clinical isolate; Bascom Palmer-Eye Institute | WT |
| Af-dsRed | Af293.1-ΔpyrG1::gdpA::dsRed::pyrG) | dsRed Fluorescence |
| Dal/CEA10 | WT-CBS144-89; Aspergillosis clinical isolate | WT |
| Ku80/CEA17 | CEA10-ΔKu80 | WT |
| Δyap1 | CEA17-Δsod1::BLE/Δsod2::PTRa/Δsod3::HPH | No Yap1 Synthesis |
| Δsod1/2/3 | CEA17-Δsod1::BLE/Δsod2::PTRa/Δsod3::HPH | No SOD1/2/3 Synthesis |
| G10 | Dal-Δnia | WT |
| ΔcatA | G10-ΔcatA::phleoR | No Catalase A |
| Δcat1/2 | G10-Δcat1::hph Δcat2::phleoR | No Catalase ½ |
| Af293 | WT-Aspergillosis Clinical Isolate | WT |
| ΔgliZ | Af293-ΔgliZ::pyrG pyrG1 | No Gliotoxin (GliZ) |
| gliZR | Af293-gliZ hygB ΔgliZ::pyrG pyrG1 | GliZ Reconstituted |
| ΔlaeA | Af293-ΔlaeA::pyrG pyrG1 | No LaeA |
| laeA OE | Af293-laeA hygB ΔlaeA::pyrG pyrG1 | LaeA Reconstituted |
| B-5233 | WT-Aspergillosis Clinical Isolate | WT |
| ΔgliP | B-5233-ΔgliP::hygB | No Gliotoxin (gliP) |
| gliPR | B-5233-gliP ΔgliP::hygB | gliP Reconstituted |
| *A. flavus* | | |
| TN-302 | Keratitis clinical isolate; Aravind Eye Hospital | WT |
| 70-GFP | *A. flavus* 70: gdp::Egfp | eGFP Fluorescence |
| NRRL3357 | WT-environmental isolate | WT |
| ΔlaeA | NRRL3357: pyrG-ΔlaeA::AfpyrG | No LaeA |
| laeA-OE | NRRL3357: pyrG-ΔlaeA::AfpyrG niaD-niaD laeA | LaeA Reconstitued |
| *F. oxysporum* | | |
| 8996 | Keratitis clinical isolate; Cleveland Clinic | WT |
| FoxL-RFP | Plant pathogen; gpd:dsRed2 | dsRed Fluorescence |
| FoxL-GFP | Plant pathogen; gpd:GFP | GFP Fluorescence |

Mouse Model of *Aspergillus* and *Fusarium* Keratitis 24, and 48 hours after infection. To inhibit thioredoxin in vivo, PX-12 (Sigma-Aldrich) was dissolved at 3 mM in a proprietary eyedrop formulation provided by Alcon and applied topically at 0 and 6 hours after infection. All animals were bred under specific pathogen-free conditions and maintained according to institutional guidelines.

Neutrophil-Specific Adoptive Transfer Mouse Model Used to Study Fungal Killing

In vivo $Cxcr2^{-/-}$ and $Cd18^{-/-}$ mice were anesthetized as described above, and conidia from a fluorescent fungal strain were injected into the corneal stroma strain (30,000 Af-dsRed conidia). At 2 hours after infection, 4 million naive BMNs isolated from the femurs and tibias of donor mice were injected intravenously into recipient mice. At 24 hours after infection, infected mice were euthanized, and fungal growth in the cornea was imaged using a fluorescence stereomicroscope. The level of fluorescence emitted from infecting fungi was quantified using image analysis software (MetaMorph, Molecular Devices; described below) and used as a measure of fungal growth during infection.

Imaging and Quantification of Light Reflected or Emitted from Infected Mouse Corneas Mice were euthanized by $CO_2$ asphyxiation and positioned in a 3-point stereotactic mouse restrainer. Corneal opacity (brightfield [BF]), fungal proliferation (RFP/GFP), cellular infiltration (GFP), and CFDA dye oxidation (GFP spectra) were visualized in the intact cornea using a high-resolution stereo fluorescence MZFLIII microscope (Leica Microsystems) and Spot RT Slider KE camera (Diagnostics Instruments). All images were obtained using the same Spot Advanced Software under the same magnification (×20), exposure (BF, 0.4 seconds; RFP, 10 seconds; eGFP, 2 seconds), gain (BF, 1; RFP/eGFP, 4/16), and gamma (BF/RFP/eGFP, 1.85) parameters. MetaMorph imaging software was used to quantify the percent area of opacity and the integrated corneal opacity.

Quantification of Aspergillus CFU

For assessment of fungal viability, whole eyes were homogenized under sterile conditions in 1 ml PBS using the Mixer Mill MM300 (Retsch) at 33 Hz for 4 minutes. Subsequently, serial log dilutions were performed and plated onto bacteriologic-grade Sabouraud dextrose agar (SDA) plates (BD). Following incubation for 24 hours at 37° C. (Aspergillus) or 30° C. (Fusarium), the number of CFU was determined by direct counting.

Identification of Fungal Growth Patterns and Neutrophil Recruitment into the Cornea Eyes were enucleated and fixed in 10% formalin in PBS (Fisher) for 24 hours. Five-micrometer sections from the center of the cornea (as determined by noncontiguous iris morphology) were cut and stained with PASH for identification of fungi and inflammatory cell recruitment. To detect infiltrating neutrophils, sections were immunostained using monoclonal rat anti-mouse neutrophil IgG (NIMP-R14, Abcam) and Alexa Fluor 488-tagged rabbit anti-rat IgG (Invitrogen). All histology slides were imaged and shown at an original magnification of ×400.

Isolation of Human Neutrophils from Peripheral Blood

Human neutrophils were isolated from normal, healthy donors using Ficoll-Paque Plus (GE) density centrifugation. Peripheral blood (20 ml) was obtained, and rbc were separated from whole blood via incubation at 1 g for 20 minutes with 3% dextran in PBS (Sigma-Aldrich). The top clear layer containing leukocytes was transferred to a fresh 50-ml conical tube and 10 ml Ficoll-Paque Plus was underlain. The cell suspension was centrifuged at 500 g for 20 minutes at 4° C. to separate mononuclear cells from neutrophils and the remaining rbc. The overlying plasma and PBMC layers were aspirated, and the neutrophil/rbc pellet was resuspended in RBC Lysis Buffer (eBioscience) (8.3 g NH4Cl, 1 g KHCO3, 0.09 g EDTA/1 l ddH2O), incubated at 37° C. for 10 minutes to lyse remaining rbc, and spun at 300 g for 5 minutes at 4° C. The lysis procedure was repeated as needed to obtain sufficient rbc lysis in cell preparations. Subsequently, cells were washed twice in PBS and ultimately resuspended in RPMI plus 1-glutamine without phenol red (Hyclone). The neutrophil cell suspension was counted using a hemocytometer, and samples were collected by Cytospin and stained by Wright-Giemsa (Fisher). Using this approach, neutrophils were routinely found to be greater than 97% of the final cell preparation.

Isolation of Peritoneal and Bone Marrow-Derived Murine Neutrophils

To isolate peritoneal neutrophils, mice were injected with 1 ml 4% thioglycolate 16 and 3 hours prior to peritoneal lavage with cold 1×PBS. Cells were transferred to a fresh 50-ml conical tube in a total volume of 30 ml, and 10 ml Ficoll-Paque Plus was underlain. Cells were then centrifuged at 1,200 g for 20 minutes at 25° C. The upper monocytic cell layer was aspirated, and the underlying neutrophil layer was washed 3 times with 50 ml PBS and resuspended in RPMI plus 1-glutamine without phenol red (Hyclone). The resulting cell suspension routinely yielded greater than 95% neutrophils. To obtain BMNs, mice were euthanized by $CO_2$ asphyxiation, and femurs and tibias were removed, cleaned, and centrifuged at 5,000 g for 45 seconds at 4° C. Contaminating rbc were lysed in 5 ml RBC Lysis Buffer, and remaining bone marrow cells were pipetted onto a discontinuous Percoll gradient (GE) of 52%, 69%, and 78%. Cells were centrifuged for 30 minutes at 1,500 g at 25° C. Following centrifugation, the neutrophils suspended in Percoll at the 69%/78% interface and below were harvested, washed twice in PBS in 50-ml conical tubes, and resuspended in RPMI medium plus 1-glutamine without phenol red. Neutrophil purity of greater than 98% was obtained routinely using this protocol.

In Vitro Neutrophil/Hypha Growth Inhibition Assay

An in vitro assay was developed to study the ability of mouse and human neutrophils to inhibit the growth of fungal hyphae from A. fumigatus, A. flavus, F. oxysporum, and F. solani species. Purified conidia (12,500/well for Aspergillus species and 100,000/well for Fusarium species) from fluorescent or non-fluorescent fungal strains were cultured in 200 µl SDA medium in black-walled 96-well plates with an optically clear bottom (CoStar 3720) until early germ tubes were observed (A. fumigatus, 6 hours; A. flavus, 4 hours; F. oxysporum, 6 hours; and F. solani, 6 hours). Wells were washed twice with sterile ddH2O and incubated 16 hours with either RPMI medium without phenol red (positive control), PBS (negative control), or RPMI with $1 \times 10^5$ murine BMNs or $2 \times 10^5$ human peripheral blood neutrophils from healthy donors. For assays in which the desired phenotype was survival of the WT fungus, $1 \times 10^5$ human neutrophils/well were used. At 16 hours after exposure, fungal growth of fluorescent strains was visualized directly using standard GFP and RFP filters in an upright microscope (Zeiss). In order to visualize and quantify fungal chitin content by non-fluorescent fungal strains, 50 µl calcofluor white stain (binds chitin; Fluka 18909) was added to each well for 5 minutes in the dark. Subsequently, plates were washed 3 times with ddH2O and imaged as stated above using standard DAPI filters or quantified via fluorometry (360/440 nm; Synergy HT; Biotek). To inhibit neutrophil NOX, we used DPI (200 µM) and Apo (30 mM). To inhibit iNOS, we used the pharmacologic inhibitors Agd (1 mM)

and SMT (100 μM). To inhibit MPO we used Indo (200 μM) and 4-AH (100 μM). All fungal growth images were taken and shown at an original magnification of ×400.

Quantification of Extracellular ROS and NO

ROS was assayed using a dye that fluoresces upon oxidation (CFDA, Invitrogen), and NO was assayed using the Griess reagent (Invitrogen). For both assays, hyphae were incubated with neutrophils in RPMI as described above for 2 hours at 37° C. and 5% $CO_2$. After 2 hours, 50 μl supernatant was transferred to wells containing either 50 μl CFDA (25 ng/ml) or 250 μl Griess reagent. For CFDA, plates were incubated in the dark for 10 minutes and read using a fluorescence spectrophotometer at excitation/emission of 485/520 nm γ (CFDA/DAF-FM). For Griess reactivity, plates were incubated in the dark for 30 minutes at 37° C., and absorbance was read at 548 nm.

Quantification of Neutrophil Intracellular ROS by Flow Cytometry

BMNs were isolated as described above and incubated with 10 μM CFDA at 37° C. for 10 minutes. CFDA-containing neutrophils ($2 \times 10^5$) were added to 96-well plates containing hyphae, and plates were spun at 300 g for 1 minute to enhance cell contact. Neutrophils were incubated at 37° C. for 1 hour, collected, and analyzed by flow cytometry (excitation/emission of 485/520 nm γ). CFDA-loaded BMNs incubated for 1 hour in empty wells were used to control for background fluorescence.

$H_2O_2$ Fungal Killing Assay

Fungi were grown for 4 hours at 37° C. in 200 μl SDB in 96-well plates as described above, and $H_2O_2$ was added at final concentrations of 1 mM-10 mM in the presence of PX-12 (0-100 μM) for an additional 2 hours. After 16 hours, fungal growth was examined by phase contrast microscopy, stained with calcofluor white, and quantified by fluorometry as described above.

Statistics

Statistical analysis was performed for each experiment using 1-way ANOVA with a Tukey post hoc analysis (Prism, GraphPad Software). A P value less than 0.05 was considered significant.

Study Approval

All animals were treated in accordance with the guidelines provided in the Association for Research in Vision and Ophthalmology (ARVO) statement for the Use of Animals in Ophthalmic and Vision Research; and protocols were approved by the Case Western Reserve University IACUC. The protocol for the use of human peripheral blood from normal healthy volunteers was approved by the Institutional Review Board of University Hospitals of Cleveland. Informed consent was obtained from each volunteer.

Results

Neutrophils have an Essential Role in Regulating Fungal Growth in the Cornea

To examine the role of neutrophils in fungal keratitis, we used two complementary approaches: systemic depletion of neutrophils from immune-competent C57BL/6 mice and adoptive transfer of neutrophils into $Cxcr2^{-/-}$ and $Cd18^{-/-}$ mice. In the first approach, neutrophils were depleted from transgenic C57BL/6 mice expressing eGFP downstream of the promoter LysM (LysM-eGFP mice) by i.p. injection of a neutrophil-specific monoclonal antibody (NIMPR-14), while control mice were given rat isotype antibody. Injection of 400 μg NIMP antibody on day 1 resulted in significantly decreased neutrophils in peripheral blood smears at 0, 24, and 48 hours after infection (S. M. Leal Jr., unpublished observations). After 24 hours, corneas were infected with conidia (40,000 in 2 μl) isolated from the A. fumigatus strain Af-dsRed, which constitutively expresses the red fluorescent protein dsRed under control of the glyceraldehydes dehydrogenase promoter. Subsequently, RFP+ fungal growth and eGFP+ neutrophil infiltration were assessed in live corneas. We also examined the effect of neutrophils on corneal opacity.

Figure 1:
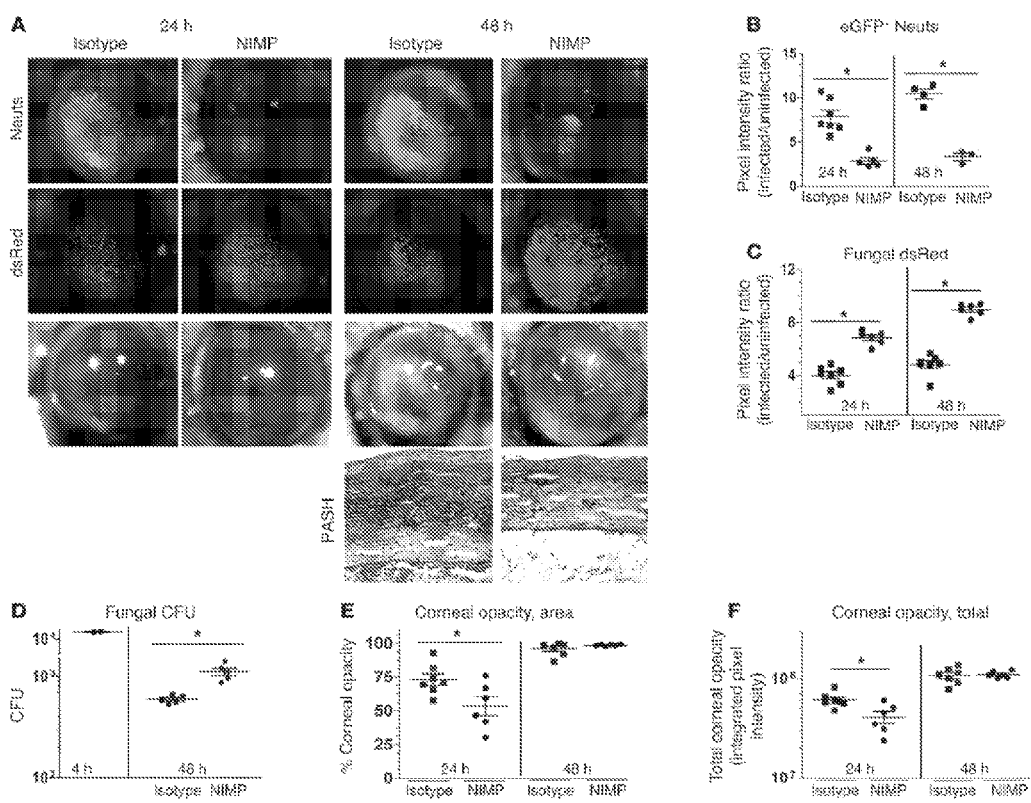
FIGS. 1(A-F) illustrate: (A) images of eyes of transgenic C57BL/6 mice with neutrophil-specific eGFP expression downstream of the lysozyme promotor (LysM) depleted of neutrophils (Neuts) with neutrophil-specific NIMPR-14 antibody (i.p.) and infected with 40,000 Af-dsRed conidia at 24 and 48 hours after infection for neutrophil infiltration (eGFP), fungal growth (dsRed), and corneal opacity (BF), the transgenic C57BL/6 mice; (B) a plot quantifying neutrophil infiltration (eGFP emission) in the mice; (C) a plot quantifying fungal dsRed expression; (D) a plot quantifying CFU in the mice eyes by direct counting; (E) a plot quantifying corneal opacity area in the mouse eyes; and (F) a plot quantifying total corneal opacity in the mouse eyes.

FIGS. 1, A and B, show-significantly increased eGFP+ neutrophils at 24 and 48 hours after infection in control, isotype-treated mice, but not in neutrophil-depleted (NIMP) mice, thus confirming neutrophil depletion in NIMP-treated mice. Conversely, FIGS. 1, A and C, shows significantly decreased dsRed-expressing fungal hyphae at 24 and 48 hours in isotype controls compared with NIMP-treated mice, which is consistent with increased CFU in NIMP-treated mice (FIG. 1D). We also found significantly lower corneal opacity in neutrophil-depleted mice as measured by both area of opacity and total corneal opacity at 24 hours but not 48 hours after infection. Corneal opacity at 48 hours was likely due to fungus-mediated tissue. FIG. 1A also shows a representative PAS-hematoxylin (PASH)-stained cornea section of a 48-hour-infected LysM-eGFP mouse with infiltrating cells in the stroma and anterior chamber, and few intact fungal hyphae. In contrast, the corneas of neutrophil-depleted mice exhibited reduced cellular infiltrates and prominent fungal hyphae in both the corneal stroma and the anterior chamber.

As a second approach, we utilized two mouse strains with known defects in neutrophil infiltration during infection and adoptively transferred WT naive bone marrow-derived neutrophils (BMNs) into these mice to study the specific role of neutrophils in killing fungi during corneal infection. $Cxcr2^{-/-}$ neutrophils are unable to recognize and respond to ELR+ CXC chemokines, whereas $Cd18^{-/-}$ neutrophils are unable to bind to ICAM-1 on limbal vessel vascular endothelial cells.

Figure 2:
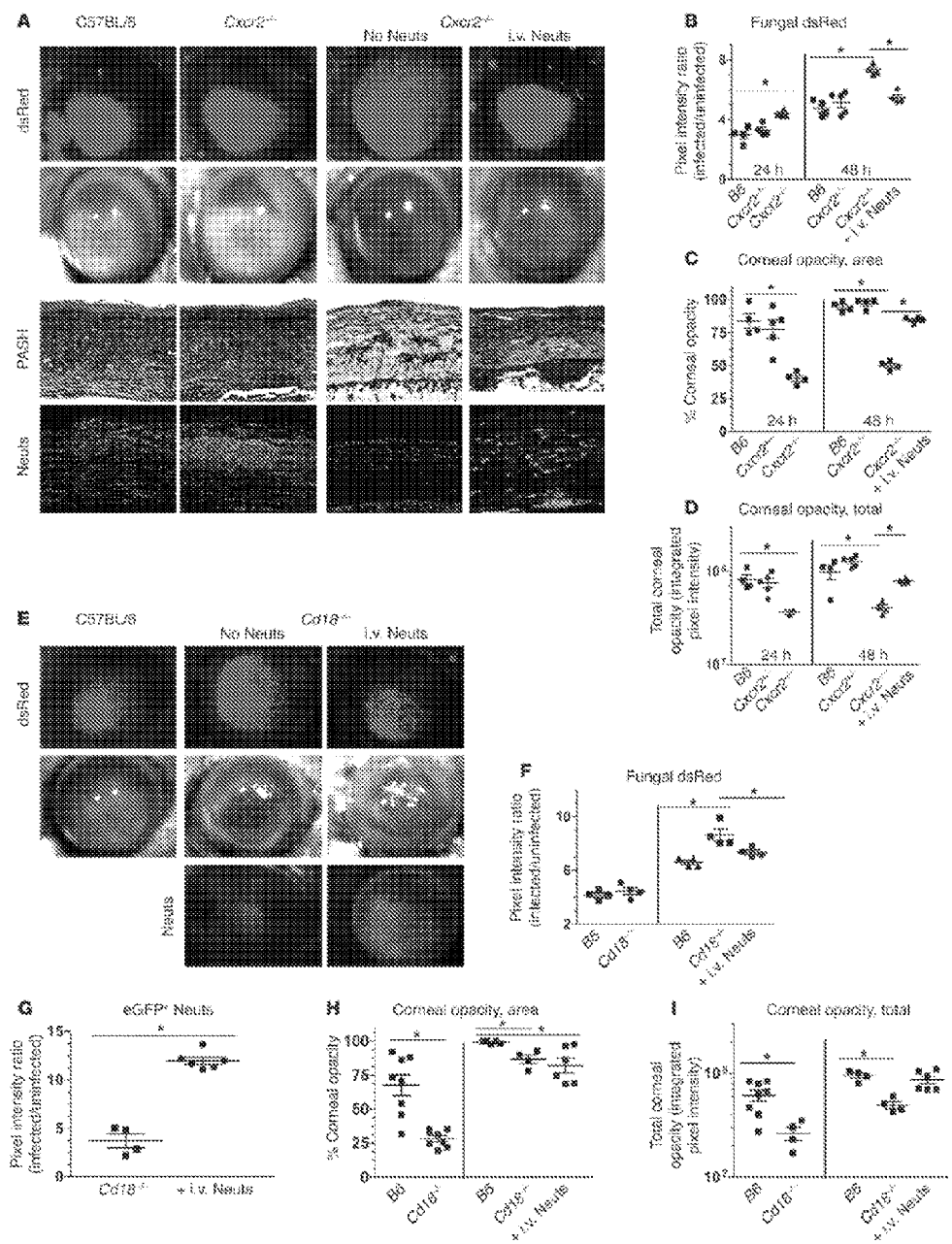
FIGS. 2(A-I) illustrate: (A) images showing corneas of C57BL/6, $Cxcr2^{+/-}$, and $Cxcr2^{-/-}$ mice eyes infected with 30,000 Af-dsRed conidia, at 24 hours after infection, one group of fungus-infected $Cxcr2^{-/-}$ mice were injected i.v. with $4\times10^6$ BMNs from C57BL/6 (B6) mice; (B) a plot quantifying fungal dsRed expression; (C) a plot quantifying corneal opacity area; (D) a plot quantifying total corneal opacity in infected corneas; (E) images of corneas of similar to $Cxcr2^{-/-}$ mice, C57BL/6 and $Cd18^{-/-}$ mice infected with Af-dsRed conidia, and at 24 hours after infection with one group of infected $Cd18^{-/-}$ mice being given 4 million adoptively transferred BMNs isolated from a LysM-eGFP mouse (eGFP+ Neuts); (F) a plot quantifying fungal dsRed expression; (G) a plot quantifying eGFP+ neutrophil infiltration; (H) a plot quantifying corneal opacity area; and (I) a plot quantifying total corneal opacity.

C57BL/6, $Cxcr2^{+/-}$, and $Cxcr2^{-/-}$ corneas were infected with A. fumigatus conidia as described above. FIG. 2A shows fungal dsRed expression and corneal opacity in C57BL/6 and $Cxcr2^{+/-}$ heterozygous mice, which both increase at 48 hours after infection. In contrast, infected $Cxcr2^{-/-}$ mice had significantly increased fungal dsRed expression (FIG. 2B) and lower corneal opacity scores (FIGS. 2, C and D) at 24 and 48 hours compared with C57BL/6 mice. However, $Cxcr2^{-/-}$ mice given C57BL/6 syngeneic neutrophils intravenously had significantly lower fungal dsRed values (FIG. 2B) and higher corneal opacity (FIGS. 2, C and D) compared with $Cxcr2^{-/-}$ mice not receiving neutrophils, indicating that neutrophils contribute to both fungal killing and corneal opacity. Corneal sections from these mice showed intense cellular infiltration, neutrophil recruitment, and minimal intact fungal hyphae at 48 hours after infection in C57BL/6 mice and $Cxcr2^{+/-}$ mice, whereas $Cxcr2^{-/-}$ corneas exhibited minimal cellular infiltrates, but abundant hyphae in the stroma and anterior chamber (FIG. 2A). Following adoptive transfer of C57BL/6 neutrophils into Cxcr2 mice, neutrophils were detected in the corneal stroma, and fungal growth in the cornea was lower than in the absence of neutrophils (FIG. 2A). Similarly, C57BL/6 neutrophils transferred to $Cd18^{-/-}$ mice during infection conferred a protective response with increased cell migration to the cornea and lower fungal load. FIGS. 2, E and F, shows that fungal dsRed expression at 48 hours was significantly increased in $Cd18^{-/-}$ mice compared with C57BL/6 mice. However, $Cd18^{-/-}$ mice given syngeneic BMNs from transgenic C57BL/6 LysM-eGFP mice exhibited significantly decreased fungal dsRed expression (FIG. 2F) along with significantly increased eGFP+ neutrophil infiltration (FIG. 2G) and increased corneal opacity (FIGS. 2, H and I).

Together, these findings demonstrate that both CXCR2 and CD18 regulate neutrophil recruitment to fungus-infected corneas and that neutrophils have an essential role in controlling fungal growth at this site.

Neutrophil NOX Activity is Required for Control of Fungal Growth During Corneal Infection NOX is an enzyme complex required for reduction of molecular $O_2$ to $O_2^-$. Superoxide is the limiting reagent in subsequent reactions, leading to the transient synthesis of ROS with greater oxidative and fungal killing potential, and individuals with CGD due to impaired NOX function are unable to control microbial infections and often succumb to filamentous fungal infections in the lung.

Figure 3:
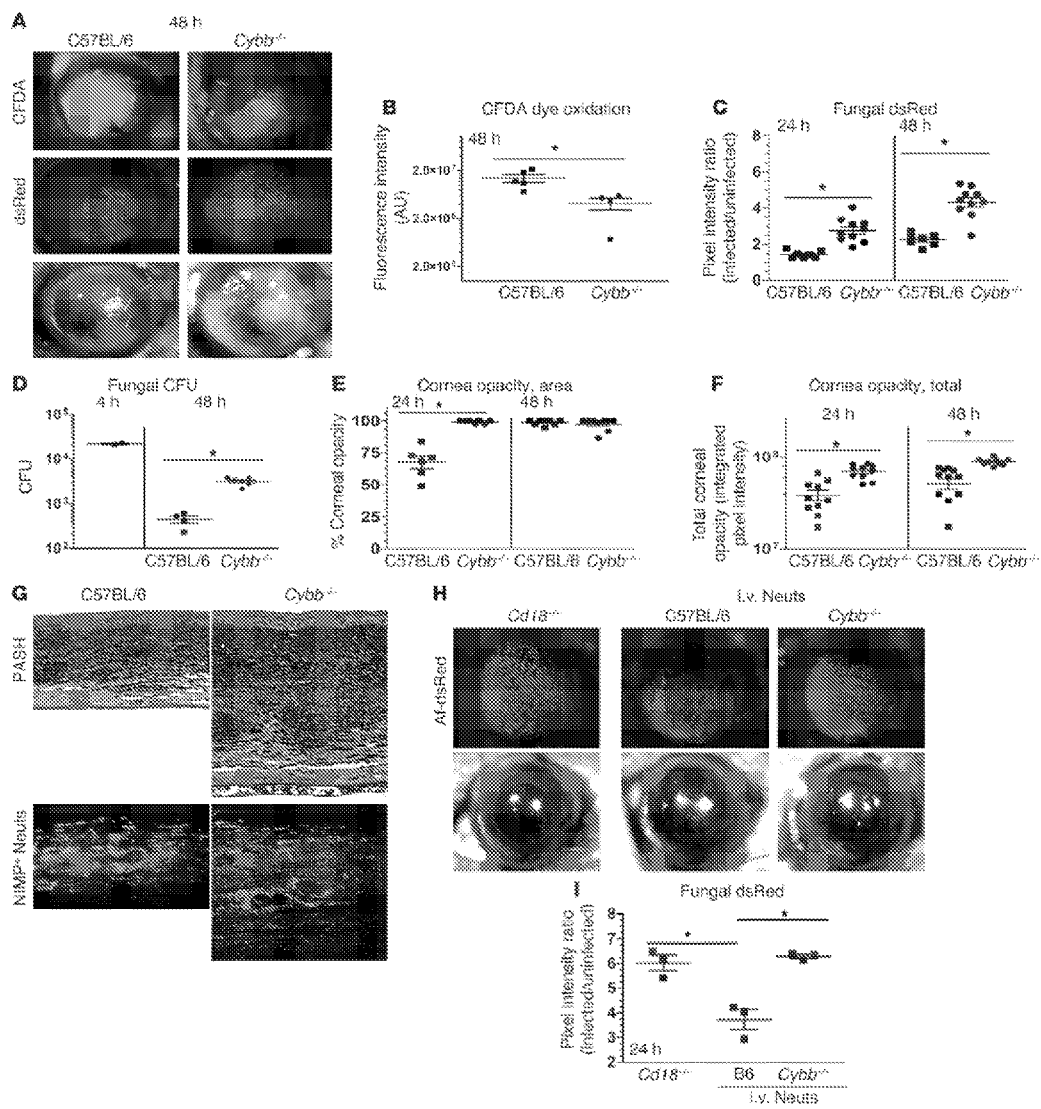
FIGS. 3(A-I) illustrate: (A) images of eyes of C57BL/6 mice and $Cybb^{-/-}$ mice infected with 40,000 *A. fumigatus* strain Af-dsRed conidia at 48 hours after infection; (B) a plot quantifying CFDA dye oxidation; (C) a plot quantifying fungal dsRed expression; (D) a plot quantifying CFU, (E) a plot quantifying corneal opacity area; (F) a plot quantifying total corneal opacity; (G) images showing 5-μm sections of 48-hour-infected fungal corneas stained with PASH or neutrophil-specific NIMP antibody; (H) images of $Cd18^{-/-}$ mice infected with *A. fumigatus* strain Af-dsRed conidia; and (I) a plot quantifying fungal dsRed expression.

$Cybb^{-/-}$ mice lack the gene encoding the NOX subunit gp91phox and thus do not express a functional NOX complex. These mice are also more susceptible to *Aspergillus* lung infections. To determine the role of NOX in fungal keratitis, we infected $Cybb^{-/-}$ mice with Af-dsRed, and ROS levels in the corneas were measured at 48 hours after infection after intrastromal injection of carboxyfluorescein diacetate (CFDA), which emits green fluorescence upon oxidation. Fungal dsRed expression and corneal opacification were measured by image analysis as described above. FIGS. 3, A and B, shows CFDA activity in C57BL/6 and $Cybb^{-/-}$ corneas at 48 hours after infection; however, total fluorescence was significantly lower in $Cybb^{-/-}$ corneas (there was no fluorescence in naïve corneas injected with CFDA; S. M. Leal Jr., unpublished observation). Conversely, fungal dsRed expression and CFU (FIGS. 3, C and D) were elevated in $Cybb^{-/-}$ compared with C57BL/6 corneas, indicating impaired fungal clearance in $Cybb^{-/-}$ corneas. Interestingly, $Cybb^{-/-}$ corneas had more severe disease than in C57BL/6 mice, with significantly higher total corneal opacity scores (FIGS. 3, E and F), which correlated with increased neutrophil infiltration and formation of microabscesses and the presence of intact fungal hyphae (FIG. 3G). As there is no defect in the ability of $Cybb^{-/-}$ neutrophils to migrate to the cornea, it is likely that these findings represent "frustrated" neutrophils that are unable to kill hyphae but can still recruit neutrophils to this site. Very similar results were found when mice were infected with other pathogenic *Aspergillus* and *Fusarium* species that cause keratitis, indicating that ROS has a more general role in inhibiting growth of filamentous fungi.

To ascertain directly whether the impaired fungal killing in $Cybb^{-/-}$ mice is due to NOX that is specifically produced by neutrophils, we infected $Cd18^{-/-}$ mice with Af-dsRed as described above and injected BMNs from C57BL/6 or $Cybb^{-/-}$ mice intravenously 2 hours after infection. Corneas were imaged 24 hours after infection. FIGS. 3, H and I, shows that fungal dsRed expression was significantly reduced following adoptive transfer of C57BL/6 neutrophils, whereas mice given $Cybb^{-/-}$ neutrophils had the same fungal dsRed expression as mice not receiving neutrophils. These data clearly demonstrate that NOX-dependent ROS production by neutrophils is essential for inhibiting fungal growth in the cornea.

iNOS and RNS are not Essential for Control of Fungal Growth

The superoxide produced by NOX can be converted to ROS or alternatively can react with NO produced by the enzymatic cleavage of arginine by iNOS, and can form the highly reactive nitrogen species (RNS) peroxynitrite (ONOO—). If iNOS activity is high and significant amounts of NO are produced, the end products of NOX activity will shift from production of ROS to production of RNS.

To test the hypothesis that RNSs are required for control of fungal growth during fungal keratitis, we injected C57BL/6 mice systemically with 1400 W, which is an irreversible pharmacologic inhibitor of iNOS. In addition, the role of iNOS was examined in gene-knockout mice.

Figure 4:
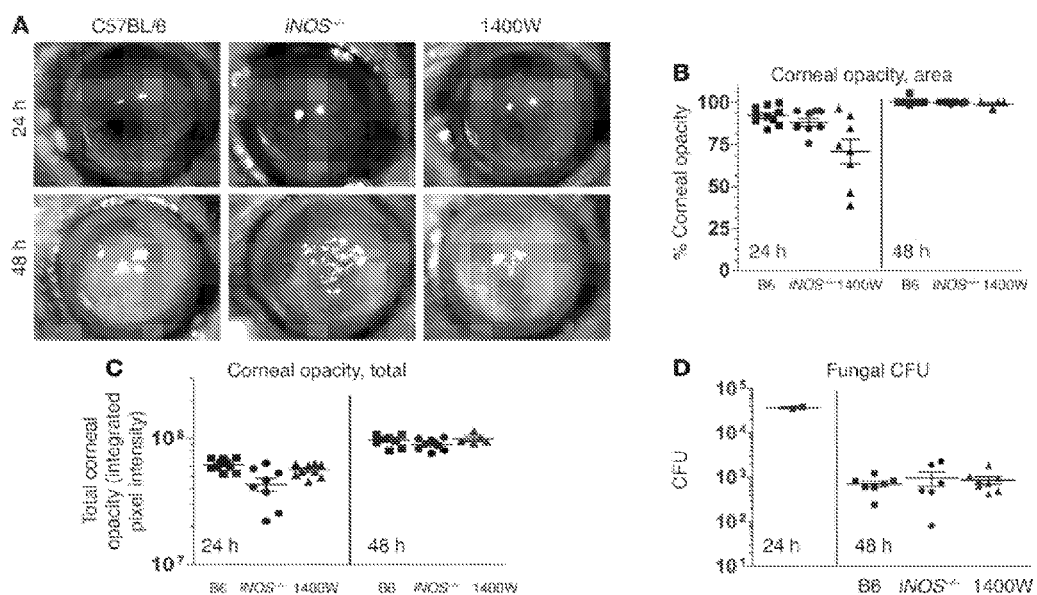
FIGS. 4(A-D) illustrate: (A) images showing eyes of C57BL/6 mice infected with *A. fumigatus* strain Af-BP conidia at 24 and 48 hours after infection; (B) a plot quantifying corneal opacity area; (C) a plot quantifying total corneal opacity; and (D) a plot quantifying CFU in infected corneas after infection.

FIG. 4 shows that there were no significant differences in corneal opacification or fungal CFU between $iNOS^{-/-}$ and C57BL/6 mice, or between untreated and 1400 W-treated C57BL/6 mice. These findings indicate that in contrast to NOX and ROS, neither iNOS nor RNS have an essential role in control of fungal growth during corneal infection.

Human and Murine Neutrophil-Mediated Killing of *A. fumigatus*, *A. flavus*, and *F. oxysporum* Hyphae is Dependent on NOX, but not iNOS or Myeloperoxidase As neutrophil NOX is required for control of fungal growth in vivo, but both conidia and hyphae are present during corneal infection, we developed a neutrophil-hypha coincubation assay to determine which neutrophil mediators are required to limit the growth of fungal hyphae. Af-dsRed, *A. flavus* eGFP, and *F. oxysporum* FoxL-GFP conidia were incubated in 96-well plates for 6 hours to allow time for germination and hyphal growth. For human neutrophil studies, neutrophils were isolated from the peripheral blood of normal volunteers and added to each well at a 16:1 ratio in the presence of pharmacological inhibitors of NOX, iNOS, or myeloperoxidase (MPO) (NOX: diphenyliodonium [DPI], apocynin [Apo]; iNOS: aminoguanidine HCl [Agd], 2-methyl-2-thiopseudoureasulfate [SMT]; MPO: indomethacin [Indo], 4-aminobenzoic hydrazide[4-AH]). For mouse neutrophil studies, neutrophils were isolated from the peritoneal cavities of C57BL/6, $Cybb^{-/-}$, and $iNOS^{-/-}$ mice and incubated with fungal hyphae as described above. Fungal growth was observed by fluorescence microscopy and measured by fluorescence spectroscopy.

Figure 5:
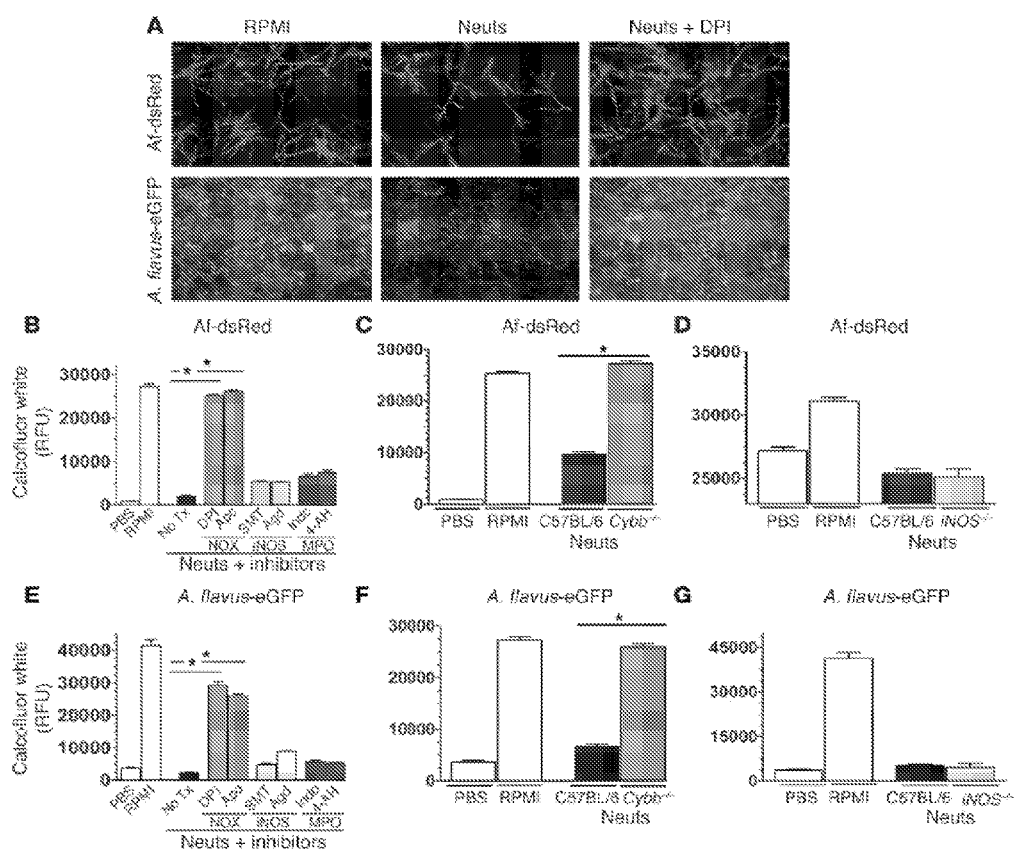
FIGS. 5(A-G) illustrate: (A) images showing fungal fluorescence of Af-dsRed and eGFP-expressing *A. flavus* (70-GFP) cultured either alone in PBS or RPMI or coincubated with $2\times10^5$ human neutrophils in RPMI or the same number of neutrophils in RPMI plus DPI; (B) a graph showing fungal calcofluor white levels and fungal chitin content of human neutrophils determined via fluorometry; (C) a graph showing calcofluor white levels and fungal chitin content of $Cybb^{-/-}$ mice; (D) a graph showing calcofluor white levels and fungal chitin content of $iNOS^{-/-}$ mice; (E) a graph showing calcofluor white levels and fungal chitin content of *A. flavus* (70-GFP) neutrophil-hypha coincubation assays with human neutrophils; and (F) $Cybb^{-/-}$ mice and (G) $iNOS^{-/-}$ mice.

FIG. 5A shows hyphal growth of *A. fumigatus* and *A. flavus* after 16 hours incubation in RPMI. However, in the presence of normal human neutrophils, fungal growth was clearly reduced, indicating that normal human neutrophils inhibit hyphal growth. However, addition of the NOX inhibitor DPI resulted in hyphal growth levels similar to that with RPMI alone, which is consistent with NOX dependent killing. FIG. 5B shows quantification of the growth of *A. fumigatus* exposed to human neutrophils for 16 hours in the presence or absence of inhibitors. Neutrophil-mediated killing was inhibited in the presence of the NOX inhibitors DPI and Apo, but not iNOS or MPO inhibitors.

As a complementary approach, we examined the role of NOX and iNOS in $Cybb^{-/-}$, $iNOS^{-/-}$, and C57BL/6 mouse neutrophils. Importantly, ROS was detected after *A. fumigatus* incubation with C57BL/6, but not $Cybb^{-/-}$, neutrophils, indicating that most of the ROS was dependent on NOX. In contrast, there was no difference in NO production between $Cybb^{-/-}$ and C57BL/6 neutrophils, and ROS production by $iNOS^{-/-}$ neutrophils was not significantly different from that by C57BL/6 neutrophils, while $iNOS^{-/-}$ neutrophils produced minimal NO.

As shown in FIG. 5C, *A. fumigatus* growth in the presence of C57BL/6 neutrophils was lower than with RPMI alone. In contrast, fungal growth after incubation with $Cybb^{-/-}$ neutrophils was significantly higher than after incubation with C57BL/6 neutrophils and similar to that after incubation with no neutrophils, and is consistent with impaired ROS activity and fungal killing. However, fungal growth was not significantly different between $iNOS^{-/-}$ and C57BL/6 neutrophils (FIG. 5D). Similar results were obtained for *A.*

*flavus* (FIGS. 5, E-G) and *F. oxysporum*. Taken together, these data indicate that inhibition of *A. fumigatus*, *A. flavus*, and *F. oxysporum* hyphal growth by human and mouse neutrophils is dependent on NOX and ROS production but not iNOS or MPO.

ROS Production and Fungal Killing are Dependent on CD18 but not Dectin-1

Figure 6:
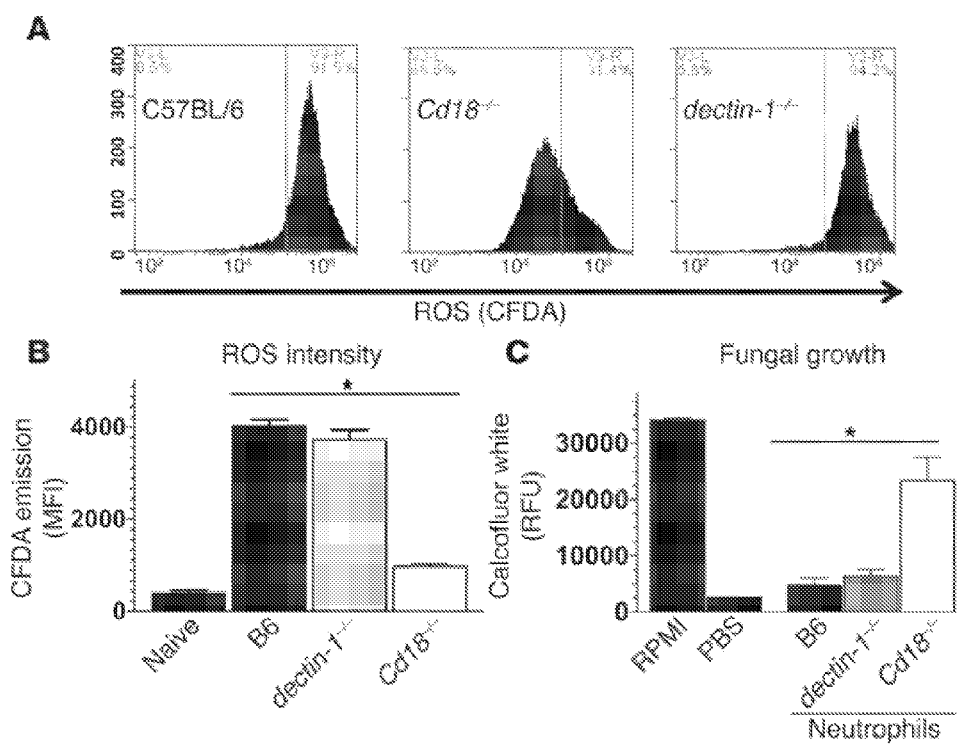
FIGS. 6(A-C) illustrate: (A) a plot showing CFDA dye oxidation analyzed by flow cytometry of C57BL/6, $Cd18^{-/-}$, and $dectin-1^{-/-}$ BMNs isolated, pre-loaded with the ROS-sensitive dye CFDA, and exposed to *A. fumigatus* hyphae for 1.5 hours; (B) a graph showing mean fluorescence intensities; and (C) a graph quantifying fungal chitin using calcofluor white of thioglycolate-elicited C57BL/6, $Cd18^{-/-}$, and $dectin-1^{-/-}$ peritoneal neutrophils, which were purified and exposed to *A. fumigatus* hyphae for 16 hours.

Activation of NOX is regulated by the physical separation of membrane and cytoplasmic components of the complex. However, following cellular activation by pathogen recognition or cytokine receptors, p47phox in the cytoplasm is phosphorylated and translocated along with other cytoplasmic NOX components to the membrane, thereby forming the functional enzyme. Dectin-1 and CD18 recognize fungal cell wall β-glucan and can activate NOX, and dectin-1$^{-/-}$ and Cd18$^{-/-}$ mice exhibit impaired fungal clearance in cornea infection models, suggesting a possible role for these receptors in neutrophil-mediated fungal killing. To examine whether these cell surface receptors mediate NOX activation and ROS production by neutrophils following exposure to fungal hyphae, we loaded naive BMNs with the ROS-sensitive dye CFDA, incubated them with *A. fumigatus* hyphae for 1 hour, and measured intracellular ROS-mediated CFDA dye oxidation using flow cytometry. FIG. 6A shows that 91.5% of C57BL/6 neutrophils and 94.2% of dectin-1$^{-/-}$ neutrophils exhibited high levels of ROS, compared with 31.4% of Cd18$^{-/-}$ neutrophils, indicating that ROS production is dependent on CD18. FIG. 6B shows mean fluorescence intensity quantification of these data.

We also examined the role of neutrophil-expressed CD18 and dectin-1 in mediating killing of fungal hyphae by coincubating *A. fumigatus* hyphae with purified thioglycolate-elicited peritoneal neutrophils from C57BL/6, Cd18$^{-/-}$, or dectin-1$^{-/-}$ mice. FIG. 6C shows significant hyphal growth at 16 hours after infection when hyphae were incubated in RPMI alone but not in PBS. These parameters were used as positive and negative controls. Hyphae coincubated with either C57BL/6 or dectin-1$^{-/-}$ neutrophils showed limited growth, whereas hyphae coincubated with Cd18$^{-/-}$ neutrophils showed significant hyphal growth similar to that observed with RPMI alone (FIG. 6C). Taken together, these findings identify a major role for CD18, but not dectin-1, in neutrophil NOX activation, ROS production, and killing of *A. fumigatus* hyphae.

*A. fumigatus* Antioxidant Resistance to Human Neutrophils is Dependent on Superoxide Dismutase and Yap1, but not Catalases, Gliotoxin, or LaeAregulated Secondary Metabolites As neutrophil NOX is essential for control of fungal growth in the cornea, and NOX is required for both human and mouse neutrophil-mediated control of hyphal growth, we hypothesize that anti-oxidative mediators produced by *Aspergillus* and *Fusarium* will scavenge ROS or inhibit NOX and thereby impair neutrophil killing.

The transcription factor Yap1 is activated in *A. fumigatus* exposed to oxidative conditions and regulates production of intracellular antioxidants and enzymes that convert ROS into less reactive products. For example, *A. fumigatus* superoxide dismutases (SOD1/2/3) convert superoxide to the less-reactive hydrogen peroxide, whereas *A. fumigatus* catalases (CatA/1/2) convert hydrogen peroxide to H$_2$O. In addition to ROS-catabolizing enzymes, filamentous fungi including *A. fumigatus* produce secondary metabolites such as gliotoxin and fumagillin, which inhibit NOX and are controlled by the master transcriptional regulator protein LaeA. We therefore examined the susceptibility of *A. fumigatus* strains with mutations in the Yap1 transcription factor (Δyap1), superoxide dismutases (Δsod1/2/3), catalases (ΔcatA, Δcat1/2), or NOX-inhibiting secondary metabolites (ΔgliP, ΔgliZ, ΔlaeA) to human neutrophils.

Figure 7:
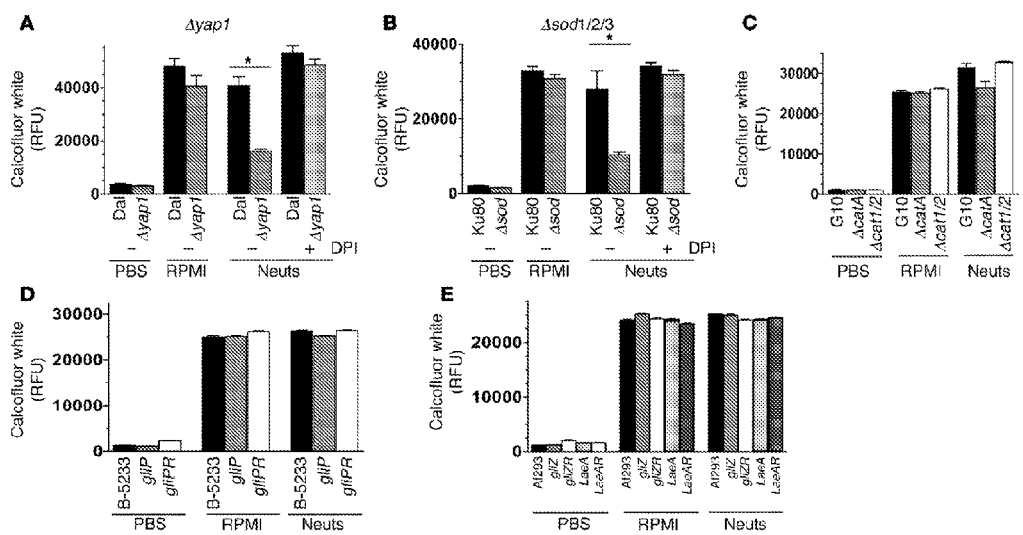
FIGS. 7(A-E) illustrate (A) a graph quantifying fungal growth by calcofluor white staining and fluorometry of Δyap1 and WT Dal1 *A. fumigatus* strains (12,500/well)

To determine whether Yap1 is required for hyphal survival in the presence of human neutrophils, we incubated Δyap1 *A. fumigates* hyphae with 1×10$^5$ human neutrophils, which are not sufficient to kill wild-type *Aspergillus* (2×10$^5$ neutrophils were used above), and measured fungal biomass by calcofluor white binding as before. FIGS. 7, A-E, shows that all WT and mutant strains grew similarly after 16 hours in RPMI medium, suggesting that there are no intrinsic growth defects in the mutant strains. FIG. 7A shows that the relative fluorescence unit (RFU) level of WT Dal hyphae grown in the presence of 1×10$^5$ human neutrophils was not significantly different from that of those grown in RPMI alone, indicating that WT Dal hyphae were not killed by 1×10$^5$ human neutrophils. In contrast, the RFU level of Δyap1 mutants (derived from WT Dal) incubated with the same number of neutrophils was significantly lower than that of WT Dal, which is consistent with increased susceptibility of Δyap1 mutants to killing by neutrophils Inhibition of neutrophil NOX using the inhibitor DPI resulted in significant growth of the Δyap1 mutant strain in the presence of neutrophils, indicating that Yap1 is required for optimal antioxidant defense against NOX-mediated oxidative stress. Similarly, the RFU level of the Δsod1/2/3 mutant was significantly lower than that of the WT Ku80 strain, and DPI treatment enabled Δsod1/2/3 mutant growth in the presence of neutrophils (FIG. 7B). However, there were no significant differences in RFU/fungal growth between ΔcatA or Δcat1/Δcat2 double mutants and WT G10 (FIG. 7C), between ΔgliP and WT B-5233 *A. fumigatus* strains (FIG. 7D), or between ΔgliZ or ΔlaeA mutants and WT Af293 (FIG. 7E).

Taken together, these data show that the anti-oxidative pathways regulated by the transcription factor Yap1 and SOD1/2/3 are essential for optimal fungal growth in the presence of human neutrophils, whereas CatA, Cat1, Cat2, gliotoxin, and LaeA-regulated secondary metabolites have either a redundant or no role in blocking neutrophil-mediated killing.

Yap1 and SOD1/2/3 are Required for Fungal Survival In Vivo

Since the *A. fumigatus* transcription factor Yap1 and SOD1/2/3 regulate the survival of hyphae in the presence of human neutrophils, we next examined the role of these mediators in corneal infection. WT or mutant conidia were injected into the corneal stroma of C57BL/6 mice, and corneal disease and fungal survival were examined as described above. We found that there was a significantly lower CFU level in corneas infected with Δyap1 mutants compared with those infected with WT Dal (FIG. 8A). These mutants also induced significantly less corneal opacity than WT Dal (FIGS. 8, B-D). Similarly, the Δsod1/2/3 mutant CFU level was significantly lower than that in WT Ku80 (FIG. 8E), although there was no detectable difference in corneal opacity (FIGS. 8, F-H).

In contrast to Δyap1 and Δsod1/2/3 mutants, and consistent with the human neutrophil studies, mice infected with ΔcatA or Δcat1/2 showed no significant differences in CFU compared with WTG10 (FIG. 8I), and there were no significant differences in CFU between corneas infected with ΔgliZ, ΔgliP, or ΔlaeA compared with either WT or reconstituted strains (FIG. 8J). Taken together, these data reveal a critical role for Yap1-regulated antioxidant pathways and SOD1/2/3 in fungal keratitis, but either a redundant or no role for catalases, gliotoxin, or LaeA-regulated secondary metabolites.

Fungal Thioredoxin Mediates Resistance to Human Neutrophils, and Oxidative Stress and is Required for Fungal Survival During Corneal Infection Exposure of *A. fumigatus* to oxidative stress activates the transcription factor Yap1, which upregulates genes involved in anti-oxidative processes. During oxidative stress, the Yap1-dependent proteins allergen aspf3 and peroxiredoxin Prx1 are highly upregulated. These are putative thioredoxin peroxidases (peroxiredoxins) in the thioredoxin antioxidant pathway, and their peroxidatic cysteine residues reduce $H_2O_2$ to $H_2O$ and are then oxidized and nonfunctional. Subsequently, thioredoxin protein reduces peroxiredoxins to their functional state, allowing further detoxification of $H_2O_2$ (44). Thioredoxin is then further reduced by the enzyme thioredoxin reductase using $H^+$ equivalents from $NADPH^+$.

Our bioinformatic analysis identified 5 putative thioredoxins encoded in the *A. fumigatus* genome (Afu5g11320/aspf29, Afu6g10300/aspf28, Afu3g14970, Afu8g01090, and Afu4g09090), two of which are known human allergens, suggesting high expression during infection. To inhibit total thioredoxin function in *A. fumigatus*, we utilized the anticancer drug PX-12 (2-[(1-methylpropyl) dithio]-1H-imidazole), which binds to the active site of thioredoxin and inhibits its ability to mediate redox reactions with target proteins and ultimately quench ROS. FIG. 9A shows that *A. fumigatus* hyphae survived incubation with sublethal doses of human neutrophils; however, upon inhibition of total thioredoxin protein with 10 μM or 100 μM PX-12, fungal growth was decreased, indicating that thioredoxin is required for hyphae survival. To determine whether PX-12 sensitizes hyphae to ROS, we grew conidia for 6 hours in SDB and incubated them with hydrogen peroxide and PX-12 (1 μM). FIG. 9B shows that 5 mM and 10 mM $H_2O_2$ killed hyphae in the presence or absence of PX-12, whereas 1 mM $H_2O_2$ alone had no effect. However, in the presence of 1 μM PX-12, this dose of $H_2O_2$ had antifungal activity. These findings demonstrate that *Aspergillus* thioredoxin mediates resistance to neutrophil and $H_2O_2$ oxidative stress.

Pharmacokinetic studies during a recent PX-12 phase I clinical trial revealed that PX-12 given at 400 $mg/m^2/d$ for 72 hours is safe to administer to patients. However, to determine whether PX-12 exhibits cytotoxicity to immune cells and cornea-specific cell types, we incubated several human myeloid and cornea cell lines for 16 hours with a dose-response curve of PX-12, at which point the release of lactate dehydrogenase (LDH) into the surrounding medium was assayed. In these assays, LDH release in the presence of PX-12 was not significantly different from that with medium alone, indicating there was no cytotoxic effect of PX-12 (S. M. Leal Jr., unpublished observations).

To determine whether thioredoxin also impairs neutrophil-mediated killing in vivo, we infected C57BL/6 mice with Af-dsRed and gave them 8-μl eyedrops of 3-mM PX-12 or vehicle at 0 and 6 hours after infection. Mice were sacrificed at 24 hours after infection and imaged. FIG. 9C shows no difference in corneal opacity between vehicle and PX-12 treatment; however, a significant reduction in fungal dsRed and CFU (FIGS. 9, D and E) was observed in PX-12-treated mice. Taken together with in vitro findings with human neutrophils and $H_2O_2$, these data clearly demonstrate that *A. fumigatus* thioredoxin proteins function as antioxidants during infection, impair neutrophil-mediated fungal killing, and are required for fungal growth during infection of the cornea.

We identified the molecular interactions between neutrophils and fungal hyphae that result in fungal death. Conclusions from these studies are illustrated in the context of neutrophil oxidase production and antioxidants produced by hyphae (FIG. 10). Unlike most leukocytes, neutrophils exhibit pronounced extracellular microbicidal activity and are likely required to kill all genera and species of pathogenic filamentous fungi. In addition, the anti-oxidative defense mechanisms shown to be important in this study are highly conserved; therefore, results from the current study are very likely relevant to fungal infections of other tissues in addition to other fungal pathogens.

Both dectin-1 and CR3 (CD11b/CD18) recognize fungal β-glucan; however, we identified an essential role for CD18, but not dectin-1, in ROS production and killing of *A. fumigatus* hyphae in vitro. These findings are consistent with observations that CR3 is the major receptor on human neutrophils for β-glucan and, more recently, that CR3 induces ROS production in response to *A. fumigatus* hyphae. The role of CD18 in neutrophil-mediated hyphal killing in vivo could not be determined in the current model due to the requirement for CD18 for neutrophil extravasation. However, we have shown that dectin-$1^{-/-}$ mice exhibit defects in fungal killing in vivo. In addition, we and others have shown that dectin-1 is required for neutrophil NOX activation in response to conidia and macrophage-mediated phagocytosis of conidia. It is therefore likely that during infection, dectin-1 on macrophages and neutrophils mediates killing of conidia, whereas CD18 on neutrophils mediates killing of hyphae.

The requisite roles for CD18 and dectin-1 in fungal killing can potentially be explained by enhanced CR3 surface expression on neutrophils compared with macrophages. Resting neutrophils and macrophages express CR3 on their surface; however, activation of neutrophils, unlike macrophages, results in progressive degranulation, CD11 b translocation to the cell surface, and CD11 b/CD18 heterodimer (CR3) formation. Alternative explanations include differences in the ability of CD18 and dectin-1 to induce granule exocytosis and translocate gp91/p22phox to the cell surface or differential CD18 and dectin-1 recognition of distinct β-glucan conformations variably expressed in hyphae and conidia. Both CR3 and dectin-1 signal through spleen tyrosine kinase (Syk), which mediates downstream activation of serine-threonine kinases (MAPKs: ERK, p38, JNK) and can potentially mediate p47phox phosphorylation and NOX activation.

In addition to the role of CD18, we reported that $Tlr4^{-/-}$, but not MD-$2^{-/-}$ $Tlr2^{-/-}$, mice exhibit increased *Aspergillus* and *Fusarium* growth during fungal keratitis, indicating an MD-2-independent role for TLR4. However, $Tlr4^{-/-}$ neutrophils killed *A. fumigatus* hyphae in vitro as efficiently as control neutrophils, indicating no role for TLR4 in hyphal killing. As TLR4 binds *A. fumigatus* galactomannan and mediates o-linked mannose-dependent recognition of *Candida albicans*, it is possible that these sugar residues are not expressed on living hyphae in sufficient number or the proper conformation to activate neutrophil TLR4. It is also possible that, since TLR4 is also activated by endogenous molecules released from lysed cells, host-mediated inflammatory products such as heat shock proteins induce TLR4 activation and TLR4-dependent fungal killing in vivo. Similar to the role of TLR4 in fungal killing in vivo, MD-2 is not required for TLR4 activation by dead cells.

CD11b/CD18 activation results in translocation of cytoplasmic NOX components to the plasma membrane and formation of a functional NOX enzyme. As illustrated in FIG. 10, NOX subsequently produces short-lived superoxide ($O_2$.) within nanometer proximity to the fungal cell wall.

$O_2$. can oxidize cell wall components directly or be converted to the more stable $H_2O_2$, and both can enter the fungal cytoplasm through porins and anion channels on the fungal plasma membrane. $H_2O_2$ can also be converted extracellularly by MPO into hypohalous acids, which are likely too short lived to enter the fungal cytoplasm or react with iNOS-derived NO forming ONOO—. Our finding that the fungal cytoplasmic antioxidant thioredoxin and superoxide dismutases, but not catalases, are essential for hyphal survival suggests that during infection, neutrophil-derived $O_2$. enters the fungal cytoplasm and along with other ROS derivatives ($H_2O_2$, etc.) mediates oxidation of essential cytoplasmic proteins and lipids, leading to death of fungal hyphae.

Using NOX-deficient $Cybb^{-/-}$ mice and adoptive transfer of $Cybb^{-/-}$ neutrophils, we demonstrate that neutrophil-specific expression of NOX and $O_2$. production are essential for controlling the growth of *A. fumigatus* in vivo. In addition, we demonstrated using specific inhibitors and gene-knockout neutrophils that NOX is required for human and murine neutrophils to kill *A. fumigatus*, *A. flavus*, and *F. oxysporum* hyphae. However, in contrast to NOX, we found no role for either iNOS or MPO in killing *Aspergillus* or *Fusarium* hyphae. Similar findings were obtained in experimental *A. fumigatus* lung infections in which NOX but not MPO or iNOS were found to be required to control fungal growth. Our findings are also in agreement with the enhanced susceptibility of CGD patients, but not MPO-deficient patients, to filamentous fungal infections. However, our findings differ from a study showing no role for NOX in killing *A. nidulans* in vitro. Given that iNOS is required for optimal intracellular killing of *Candida* and *Cryptococcus* yeasts, and that MPO is required for optimal responses to *Candida*, it is possible that these enzymes are more effective against intracellular yeast rather than extracellular hyphae.

FIG. 10 also illustrates fungal antioxidant pathways. Oxidation by neutrophils induces nuclear translocation of Yap1, as well as upregulation of the $H_2O_2$-catabolizing thioredoxin-dependent peroxiredoxin aspf29 and prx and secreted Cat1/2. The current study identified the Yap1 transcription factor as essential for hyphal survival during corneal infection and following exposure to neutrophils. These findings are in agreement with the results of a report on *C. albicans* in which the Yap1 homolog Cap1p was required for anti-oxidative defenses. However, our results differ from *A. fumigatus* lung infection studies that showed no role for Yap1 during infection of immunocompromised mice or after exposure of neutrophils to swollen conidia. These differences are likely explained by differences in the immune status of the infected mice, although there may also be a morphotype-specific role for Yap1.

In the current studies we did not detect a role for Yap1-regulated and -secreted Cat1/2 or for cytoplasmic CatA in hyphal survival. These findings are consistent with studies on experimental *Aspergillus* lung infection and are likely due to the lack of CatA expression in hyphae as opposed to conidia and the unavailability of secreted Cat1/2 for cytoplasmic antioxidant defense by hyphae. Further, Yap1 induces high levels of intracellular peroxiredoxins following oxidative stress, and similar to catalases, peroxiredoxins reduce $H_2O_2$ to $H_2O$ and are then oxidized. Subsequently, peroxiredoxins are cyclically reduced to their functional state by thioredoxin protein, which is itself reduced by thioredoxin reductase. The importance of thioredoxin protein in fungal antioxidant defense is evidenced by (a) elevated *A. fumigatus* thioredoxin reductase expression found after exposure to normal versus CGD neutrophils; and (b) the essential role of thioredoxin in antioxidative responses in *A. nidulans*. In the current study, bioinformatic analysis revealed 5 putative thioredoxins in the *A. fumigatus* genome, including the human allergens aspf29 and aspf28, which are highly expressed during human infection. We constructed a single-knockout strain of aspf29 and did not observe a difference in fungal survival in vivo, likely due to redundancy by the other 4 putative thioredoxins encoded in the *A. fumigatus* genome (S. M. Leal Jr., unpublished observations). We therefore utilized PX-12 to inhibit all 5 putative thioredoxins and showed that thioredoxin is required for hyphal survival in the presence of neutrophils in vitro and that PX-12 enhances $H_2O_2$-mediated killing (FIG. 9 *a*). Further, we found that topical application of PX-12 was sufficient to restrict fungal growth in vivo, thereby indicating that this or similar compounds that target the thioredoxin pathway can block fungal thioredoxins and inhibit the predominant antioxidant defense utilized by these pathogens during infection.

FIG. 10 also illustrates that *A. fumigatus* produces 3 superoxide dismutases that catalyze the conversion of superoxide to $H_2O_2$. SOD1 and SOD3 are both cytoplasmic, whereas SOD2 is restricted to the mitochondrial membrane. In this study, we identified a role for the superoxide dismutases in mediating hyphal survival during oxidation by neutrophils and during infection. Our findings are consistent with increased cytoplasmic SOD1 and SOD3 but not mitochondrial SOD2 expression by *A. fumigatus* hyphae in the presence of normal versus CGD neutrophils and the increased susceptibility of *A. fumigatus* Δsod1/2/3 mutants to killing by alveolar macrophages. However, Δsod1/2/3 mutants showed no difference in survival in an immunocompromised lung infection model. Given that SOD3 is the most highly expressed SOD in hyphae under oxidative conditions, it is likely that SOD3 is functionally dominant in *A. fumigates* hyphae.

Lastly, although secondary metabolites upregulated by the LaeA transcription factor are reported to have immunosuppressive effects, including gliotoxin, fumagillin, fumagatin, and helvolic acid, we did not detect a role for these toxins in hyphal survival following exposure to neutrophils or during infection. Given that secondary metabolite production by *A. fumigatus* in culture peaks at 48 hours after infection, it is possible that secondary metabolites may mediate fungal survival in patients, but not mice, due to the more chronic nature of human disease—typically weeks to months—compared with our acute murine model of fungal keratitis.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, we claim:

1. A method of treating a fungal infection in a subject comprising:
    administering to the subject a therapeutically effective amount of a disulfide thioredoxin protein inhibitor to treat the fungal infection in the subject, the thioredoxin protein inhibitor comprising a small molecule having a molecular weight of less than about 350 g/mole, the thioredoxin inhibitor including an asymmetrical or symmetrical disulfide having the formula $R_1$—S—S—

Y—S—S—R$_2$, wherein R$_1$, R$_2$, and Y are each independently selected from the group consisting of a substituted or unsubstituted alkyl, arylalkyl, imidazole, thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone; and pharmaceutically acceptable salts thereof.

2. The method of claim 1, the therapeutically effective amount of a thioredoxin protein inhibitor comprising an amount effective to inhibit the YAP1-regulated thioredoxin anti-oxidative stress response in a fungal cell in the subject.

3. The method of claim 1, the fungal infection being selected from the group consisting of corneal, lung, skin/nail, mucosal, systemic fungal infections and combinations thereof.

4. The method of claim 1, the fungal infection selected from an *Alternaria, Aspergillus, Candida, Curvularia, Fusariu*, or *Histoplasma* fungal infection.

5. The method of claim 1, the fungal infection comprising a corneal fungal infection.

6. The method of claim 5, the corneal fungal infection comprising a corneal fungal infection related to *Aspergillus, Fusarium, Curvularia*, or *Alternaria*.

7. The method of claim 5, the corneal fungal infection associated with corneal inflammation.

8. The method of claim 1, the subject not having a fungal infection, but being at risk of developing a fungal infection.

9. The method of claim 1, wherein the subject is a neutropenic subject.

10. The method of claim 1, the thioredoxin protein inhibitor being administered to the subject topically.

11. The method of claim 1, the thioredoxin protein inhibitor being administered to the subject in an ophthalmic preparation.

12. The method of claim 1, the thioredoxin protein inhibitor being administered to the subject in conjunction with one or more additional therapeutic agents.

13. The method of claim 12, the one or more additional therapeutic agents comprising a fungal iron acquisition inhibitor, antibiotic, antiviral or antifungal agent.

14. The method of claim 13, the fungal iron acquisition inhibitor selected from the group consisting of an iron chelator, a siderophore binding protein, and a siderophore biosynthesis inhibitor.

15. A method of treating a fungal infection in a subject comprising:
topically administering to the subject a therapeutically effective amount of a disulfide thioredoxin protein inhibitor to treat fungal infection in the subject, the thioredoxin protein inhibitor comprising a small molecule having a molecular weight of less than about 350 g/mole and
a fungal iron acquisition inhibitor selected from the group consisting of an iron chelator, a siderophore binding protein, and a siderophore biosynthesis inhibitor.

16. The method of claim 15, the thioredoxin inhibitor including an asymmetrical or symmetrical disulfide having the formula R$_1$—S—S—R$_2$, wherein R$_1$ and R$_2$ are each selected from the group consisting of a substituted or unsubstituted alkyl, arylalkyl, imidazole, thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone; and pharmaceutically acceptable salts thereof.

17. The method of claim 15, the thioredoxin inhibitor including an asymmetrical or symmetrical disulfide having the formula R$_1$—S—S—Y—S—S—R$_2$, wherein R$_1$, R$_2$, and Y are each independently selected from the group consisting of a substituted or unsubstituted alkyl, arylalkyl, imidazole, thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, or cycloalkanone; and pharmaceutically acceptable salts thereof.

18. The method of claim 15, the thioredoxin protein inhibitor including an asymmetric disulfide compound having the general formula (I):

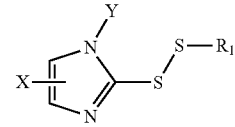

(I)

or a pharmaceutically acceptable salt thereof,
wherein R$_1$ and Y are each independently selected from the group consisting of a hydrogen, a substituted or unsubstituted alkyl, arylalkyl, imidazole thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone; and wherein X is selected from the group consisting of hydrogen, alkyl, alkoxy, hydroxyl, carboxy, carbaldehyde, amino, halo, keto, nitro and combinations thereof.

19. The method of claim 15, the thioredoxin protein inhibitor of formula (I) having the formula:

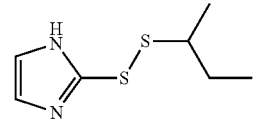

or a pharmaceutically acceptable salt thereof.

20. The method of claim 15, the therapeutically effective amount of a thioredoxin protein inhibitor comprising an amount effective to inhibit the YAP1-regulated thioredoxin anti-oxidative stress response in a fungal cell in the subject.

21. The method of claim 15, the corneal fungal infection comprising a corneal fungal infection related to *Aspergillus, Fusarium, Curvularia*, or *Alternaria*.

22. The method of claim 15, the thioredoxin protein inhibitor being administered to the subject in an ophthalmic preparation.

23. The method of claim 15, the thioredoxin protein inhibitor and fungal iron acquisition inhibitor being administered to the subject in conjunction with one or more additional therapeutic agents.

24. The method of claim 23, the one or more additional therapeutic agents comprising a fungal iron acquisition inhibitor, antibiotic, antiviral or antifungal agent.

* * * * *

UNITED STATES PATENT AND TRADEMARK OFFICE
CERTIFICATE OF CORRECTION

PATENT NO. : 9,603,839 B2
APPLICATION NO. : 14/395377
DATED : March 28, 2017
INVENTOR(S) : Eric Pearlman et al.

Page 1 of 1

It is certified that error appears in the above-identified patent and that said Letters Patent is hereby corrected as shown below:

In the Specification

Column 1, Line 14 reads "18612" should read --018612--

Signed and Sealed this
Fifth Day of December, 2017

Joseph Matal
*Performing the Functions and Duties of the
Under Secretary of Commerce for Intellectual Property and
Director of the United States Patent and Trademark Office*

UNITED STATES PATENT AND TRADEMARK OFFICE
CERTIFICATE OF CORRECTION

PATENT NO. : 9,603,839 B2
APPLICATION NO. : 14/395377
DATED : March 28, 2017
INVENTOR(S) : Eric Pearlman and Sixto M. Leal Page 1 of 1

It is certified that error appears in the above-identified patent and that said Letters Patent is hereby corrected as shown below:

In the Specification

Please replace the following paragraph starting at Line 11, Column 1 with:
--GOVERNMENT FUNDING
This invention was made with government support under grant EY018612 awarded by the National Institutes of Health. The government has certain rights in the invention.--

This certificate supersedes the Certificate of Correction issued December 5, 2017.

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*